US012758947B2

(12) United States Patent
Miller et al.

(10) Patent No.: US 12,758,947 B2
(45) Date of Patent: Oct. 13, 2026

(54) ZINC(II) AND GALLIUM(III) CATALYSTS FOR OLEFIN REACTIONS

(71) Applicant: PURDUE RESEARCH FOUNDATION, West Lafayette, IN (US)

(72) Inventors: Jeffrey T. Miller, Naperville, IL (US); Nicole Libretto, Lakewood, CO (US); Christopher Russell, West Lafayette, IN (US); Matthew A. Conrad, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 172 days.

(21) Appl. No.: 18/330,538

(22) Filed: Jun. 7, 2023

(65) Prior Publication Data

US 2023/0330633 A1 Oct. 19, 2023

Related U.S. Application Data

(62) Division of application No. 17/109,515, filed on Dec. 2, 2020, now abandoned.

(Continued)

(51) Int. Cl.

*B01J 23/06* (2006.01)
*B01J 23/08* (2006.01)

(Continued)

(52) U.S. Cl.

CPC ............... *B01J 23/06* (2013.01); *B01J 23/08* (2013.01); *B01J 29/005* (2013.01); *B01J 35/613* (2024.01);

(Continued)

(58) Field of Classification Search

CPC ... B01J 23/06; C07C 2/10; C07C 2/12; C07C 2521/08; C07C 2523/06

See application file for complete search history.

(56) References Cited

U.S. PATENT DOCUMENTS 5,849,972 A * 12/1998 Vicari .................... B01J 23/755 585/533
9,192,919 B2 11/2015 Hock (Continued)

FOREIGN PATENT DOCUMENTS

AU 2015227408 A1 * 10/2015
CN 101332432 A * 12/2008

(Continued)

OTHER PUBLICATIONS

Schweitzer et al., (Propylene Hydrogenation and Propane Dehydrogenation by a Single-Site Zn2+ ion on Silica Catalyst, ACS Catal. 2014, 4, 1091-1098).

(Continued)

*Primary Examiner* — Jun Li

(74) *Attorney, Agent, or Firm* — Edmonds & Omaidalka, P.C.

(57) ABSTRACT

Oligomerization catalyst and method for oligomerization using the catalyst. The catalyst comprises a single Zn(II) or Ga(III) metal ion center directly bonded to a support through a shared oxygen atom, the catalyst having at least one M-O bond which forms an active site for oligomerization. The method includes reacting one or more C2 to C12 olefins with the oligomerization catalyst at a temperature of about 200° C. or higher to provide an oligomer product comprising C4 to C26 olefins.

20 Claims, 16 Drawing Sheets

Related U.S. Application Data

(60) Provisional application No. 62/942,973, filed on Dec. 3, 2019.

(51) Int. Cl.

| | |
|---|---|
| ***B01J 29/00*** | (2006.01) |
| ***B01J 35/10*** | (2006.01) |
| ***B01J 35/61*** | (2024.01) |
| ***B01J 35/64*** | (2024.01) |
| ***C07C 2/10*** | (2006.01) |

(52) U.S. Cl.

CPC ........... *B01J 35/615* (2024.01); *B01J 35/617* (2024.01); *B01J 35/643* (2024.01); *C07C 2/10* (2013.01); *B01J 2235/00* (2024.01); *C07C 2523/06* (2013.01); *C07C 2523/08* (2013.01)

(56) References Cited

U.S. PATENT DOCUMENTS

| | | | | |
|---|---|---|---|---|
| 2002/0077431 | A1* | 6/2002 | Whiteker | C08F 210/16 526/172 |
| 2012/0283494 | A1 | 11/2012 | Smith | |
| 2014/0275686 | A1* | 9/2014 | Hock | B01J 23/755 502/259 |
| 2016/0074838 | A1 | 3/2016 | Hock | |
| 2019/0144357 | A1* | 5/2019 | Kardash | C07C 2/36 585/16 |
| 2020/0055797 | A1* | 2/2020 | Deimund | B01J 29/7661 |
| 2020/0056106 | A1* | 2/2020 | Deimund | B01J 29/7261 |
| 2021/0129121 | A1* | 5/2021 | Gounder | B01J 29/7057 |

FOREIGN PATENT DOCUMENTS

| | | | | | |
|---|---|---|---|---|---|
| CN | 108273543 | A | * | 7/2018 | B01J 29/48 |
| CN | 110201713 | A | * | 9/2019 | B01J 31/0288 |
| JP | 3749756 | B2 | * | 3/2006 | |
| JP | 3937200 | B2 | * | 6/2007 | |
| JP | 4108141 | B2 | | 6/2008 | |
| JP | 4870891 | B2 | * | 2/2012 | C08F 10/02 |
| WO | WO-2009073395 | A1 | * | 6/2009 | B01J 29/185 |
| WO | WO-2019028035 | A2 | * | 2/2019 | C07C 2/12 |

OTHER PUBLICATIONS

Chen et al. (ZnO Nanoclusters Supported on Dealuminated Zeolite • as a Novel Catalyst for Direct Dehydrogenation of Propane to Propylene, ChemCatChem, 2019, 11, 868-877).

* cited by examiner

ZINC(II) AND GALLIUM(III) CATALYSTS FOR OLEFIN REACTIONS

CROSS-REFERENCE TO RELATED APPLICATIONS

This application is a divisional of U.S. patent application Ser. No. 17/109,515, filed on Dec. 2, 2020, which claims priority to U.S. Provisional Patent Application Ser. No. 62/942,973, filed on Dec. 3, 2019, all of which are incorporated by reference herein in their entireties.

GOVERNMENT LICENSE RIGHTS

This invention was made with government support under Cooperative Agreement No. EEC-1647722 awarded by the National Science Foundation. The government has certain rights in the invention.

BACKGROUND

Field of the Invention

Embodiments of the present invention generally relate to light hydrocarbon alkene oligomerization. More particularly, embodiments relate to catalyst development for light hydrocarbon alkene oligomerization.

Description of the Related Art

The oligomerization of olefins is of high academic and industrial interest because it leads to the building blocks of industrial and consumer products including plastics, detergents, lubricants, petrochemicals, and a variety of industrial chemicals. Oligomerization is the process by which short chain olefins (like ethylene ($C_2H_4$) and propylene ($C_3H_6$)) are converted to intermediate chain-length olefins. This chain growth depends on the number of reacting molecules. For example, in $C_2H_4$ oligomerization, at low conversions, two $C_2H_4$ molecules combine to form butenes ($C_4H_8$), but low molar concentrations of $C_4H_8$ inhibits further chain growth. At higher conversions, i.e. when enough $C_4H_8$ is produced, the $C_4H_8$ molecules can either combine with $C_2H_4$ or another $C_4H_8$ to form hexenes ($C_6H_{12}$) or octenes ($C_8H_{16}$) and so on. If only oligomerization occurs with an even number carbon reactant, then only products containing even numbers of carbons are possible. Similarly, $C_3H_6$ oligomerization would yield a normal distribution of hexenes ($C_6H_{12}$), nonenes ($C_9H_{18}$) and so on.

The conversion of short chain olefins (formed from steam cracking, fluid catalytic cracking, dehydrogenation, Fischer Tropsch processes, etc.) to long chain hydrocarbons, has been of considerable interest in the past. Fuel products have been produced by oligomerization since the early 1930s. Linear alpha olefins, which can be produced by ethylene oligomerization, are also of interest in the petrochemical industry, where millions of tons are produced annually. Oligomerization is a necessary step to produce the precursors for many consumer products.

Current commercial oligomerization processes utilize homogeneous catalysts including nickel (Ni), Titanium (Ti), Zirconium (Zr), and Chromium (Cr), which show high activity and selectivity towards linear alpha olefins. For example, the Shell Higher Olefin Process (SHOP) utilizes Ni-based organometallic complexes, bearing a chelating ligand with a neutral phosphine and an anionic oxygen donor. The critical discovery by Karl Ziegler and Heinz Martin that Titanium Chloride, in combination with Aluminum Ethyl Chloride $Al(C_2H_5)_2Cl$ catalyzes the conversion of ethylene to 1-butene with high selectivity, paved the way for the Ziegler type of catalysts. Various combinations of these have been used for the development of commercial processes. For example, the Alphabutol process is used to convert ethylene to 1-butenes with Ti catalysts. This is also performed using Zr-alkoxides, which have lower activity, but comparable selectivity. The Gulfene and Ethyl processes by Chevron Phillips and Ineos respectively also utilize these catalysts. The relatively newer processes by IFP Energies nouvelles (IFPEN) and SABIC-Linde developed processes based on a Ziegler catalytic system composed of a Zirconium precursor, a ligand, and an Aluminum co-catalyst.

Cr-based catalysts can also be used for ethylene trimerization to produce 1-hexene. For example, the Phillip's catalyst, $Cr/SiO_2$, is the only catalyst that can perform this commercially and is responsible for producing 47000 tons per annum of 1-hexene.

After the commercial uses of Ni and Cr, other transition metal catalysts involving cobalt (Co) and iron (Fe) have also been explored as potential oligomerization catalysts, but the catalysts require activation with additional ligands. Current homogeneous oligomerization catalysts require the use of catalyst activators, as well as additional separation steps to recover and regenerate the catalysts, both of which are economically and practically infeasible.

To address this, the heterogeneous counterparts have been extensively studied on a variety of metals and supports. Among many transition metals utilized for ethylene oligomerization, nickel supported on silica, silica-alumina and various zeolites have shown high activity.

Oligomerization follows a well-known coordination insertion mechanism. An alkyl chain grows by coordination of the olefin to a vacant site on the metal center, and then subsequent formation of the metal alkyl bond by alkylation of a metal hydride. Desorption of the olefin product can take place by beta hydride elimination or transfer, restoring the metal hydride site and leaving a surface hydroxyl group on $SiO_2$. Typically, oligomerization processes are operated at low temperatures (150° C. to 250° C.) and high pressures (0.5 atm-15 atm) in batch and flow reactors. High temperature (>300° C.) oligomerization processes have not been proven economically.

There is a need, therefore, for new and improved oligomerization catalysts capable of oligomerization at acceptable conversion rates at higher reaction temperatures.

SUMMARY

An oligomerization catalyst, oligomer products and methods for making and using the same are provided. The catalyst can include Zn(II) or Ga(III) based compounds that are stable at oligomerization temperatures of 200° C. or higher. The catalyst is particularly useful for making oligomers containing C4 to C26 olefins having a boiling point in the range of 170° C. to 360° C., which can be used to produce diesel and jet fuels.

In one or more embodiments, the oligomerization catalyst includes a single Zn(II) or Ga(III) metal ion center directly bonded to a support through a shared oxygen atom. The active catalyst forms up to four M-O bonds, where at least one M-O bond provides an active site for oligomerization.

In one or more embodiments, the method for oligomerization includes reacting one or more C2 to C12 olefins with the oligomerization catalyst(s) at a temperature of about 200° C. or higher to provide an oligomer product comprising C4 to C26 olefins.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are, therefore, not to be considered limiting of its scope, for the invention may admit to other equally effective embodiments.

DETAILED DESCRIPTION

Figure 1A:
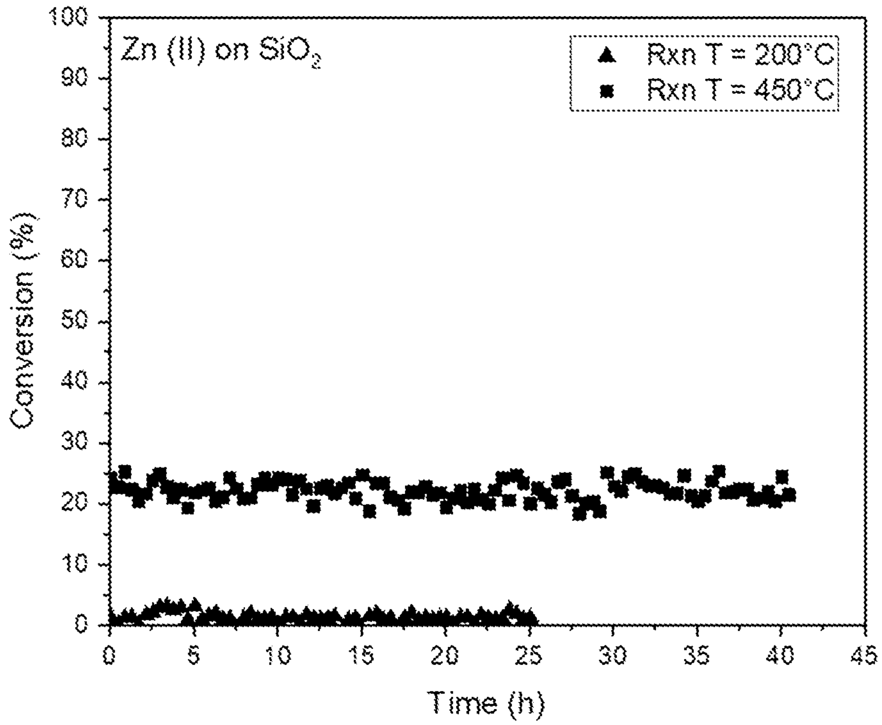
FIG. 1A shows the conversion (%) of supported Zn(II) on silica catalysts as a function of time in ethylene oligomerizations at 200° C. and 450° C.

It is to be understood that the following disclosure describes several exemplary embodiments for implementing different features, structures, and/or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. Moreover, the exemplary embodiments presented below can be combined in any combination of ways, i.e., any element from one exemplary embodiment can be used in any other exemplary embodiment, without departing from the scope of the disclosure.

Certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name, but not function. Furthermore, in the following discussion and in the claims, the terms "including" and "comprising" are used in an open-ended fashion, and, thus, should be interpreted to mean "including, but not limited to." The phrase "consisting essentially of" means that the described/claimed composition does not include any other components that will materially alter its properties by any more than 5% of that property, and in any case, does not include any other component to a level greater than 3 wt %.

Unless otherwise indicated, all numerical values are "about" or "approximately" the indicated value, meaning the values take into account experimental error, machine tolerances and other variations that would be expected by a person having ordinary skill in the art. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

In accordance with one or more embodiments described herein, a zinc-based catalyst and a gallium-based catalyst for olefin oligomerization at high temperatures are provided. It has been surprisingly and unexpectedly discovered that oligomerization can be achieved at high reaction temperatures, such as 200° C. to 450° C., using the zinc-based catalyst or gallium-based catalyst described herein. The zinc surprisingly and unexpectedly remains in the +2 oxidation state at reaction temperatures at or above 200° C., and exhibits high stability and activity for light hydrocarbon oligomerization. The gallium also surprisingly and unexpectedly remains in the +3 oxidation state at reaction temperatures at or above 200° C., and exhibit high stability and activity for light hydrocarbon oligomerization. These catalysts also exhibit significantly improved activity over a wide range of oligomerization pressures, such as 1 atm to 35 atm.

It has also been surprisingly discovered that the zinc-based catalyst and the gallium-based catalysts provided herein have catalyst activity that increases with temperature and pressure. At oligomerization temperatures of 200° C. or more, the catalysts provided herein are highly stable and can also be regenerated. These catalysts are suitable for producing C4H8 oligomers as well as small amounts of products of CH4, C2H6, and C3H6 due to secondary olefin reactions.

By "oligomer(s)", it is meant dimers, trimers, tetramers, and other molecular complexes having less than 26 repeating units. Oligomers provided herein are typically gases or liquids at ambient temperature, and can include low melting solids, including waxes, at ambient temperature. In some embodiments, the oligomers provided herein can have an atomic weight or molecular weight of less than 10,000 AMU (Da), such as about 5,000 or less, 1,000 or less, 500 or less, 400 or less, 300 or less, or 200 or less. The molecular weight of the oligomer, for example, can range from a low of about 50, 250 or 350 to a high of about 500, 3,000, 7,000, or 9,000 AMU (Da).

The zinc and gallium catalysts do not require a co-catalyst or activator to create a reactive site that will coordinate, insert, and oligomerize the olefin(s); however, any one or more co-catalyst or activators can be used. As used herein, the terms "cocatalyst" and "activator" are used herein interchangeably and refer to any compound, other than the reacting olefin, that can activate the zinc- or gallium-based catalyst by converting the neutral catalyst compound to a catalytically active catalyst compound cation. For example, the following co-catalyst and/or activators can optionally be used: alumoxanes, aluminum alkyls, ionizing activators, which may be neutral or ionic, alumoxane compounds, modified alumoxane compounds, and ionizing anion precursor compounds that abstract one reactive, σ-bound, metal ligand making the metal complex cationic and providing a charge-balancing noncoordinating or weakly coordinating anion.

The catalyst can be deposited on, contacted with, bonded to, or incorporated within, adsorbed or absorbed in, or on, any one or more suitable support materials or carriers. For example, a suitable support material or carrier can be a porous support material, such as an inorganic oxide. Suitable support materials can further include silica, which may or may not be dehydrated, fumed silica, alumina, silica-alumina or mixtures thereof. Other suitable support materials can include magnesia, titania, zirconia, montmorillonite, phyllosilicate, clays and the like. Other suitable support materials can include nanocomposites and aerogels. Other suitable support materials can include silicon dioxide, aluminum oxide, titanium dioxide, zeolites, silica-alumina, cerium dioxide, zirconium dioxide, magnesium oxide, silica pillared clays, metal modified silica, metal oxide modified silica, metal oxide modified silica-pillared clays, silica-pillared micas, metal oxide modified silica-pillared micas, silica-pillared tetrasilicic mica, silica-pillared tainiolite, and combinations thereof. Suitable zeolite supports can be or can include ZSM-5, BEA, MOR, Y, AlPO-5, and the like.

Combinations of any two or support materials can be used, for example, silica-chromium, silica-alumina, silica-titania and the like. The foregoing supports are commercially available or can be prepared using techniques known to those skilled in the catalysis art.

The catalyst can contain zinc and/or gallium in any amount sufficient to make the oligomer(s) described. For example, the amount of zinc and/or gallium can be about 0.1 wt % to about 20 wt %, or about 0.1 wt % to about 10 wt %, or about 0.1 wt % to about 8 wt %, or about 0.1 wt % to about 5 wt %, or about 0.1 wt % to about 3 wt %, or about 2.4 wt %, or about 2.5 wt %, or about 2.6 wt %, or about 2.7 wt %, or about 2.8 wt %, based on the total weight of the catalyst.

The support material can have a surface area in the range of from about 10 $m^2/g$ to about 700 $m^2/g$, a pore volume in the range of from about 0.1 cc/g to about 4.0 cc/g and an average particle size in the range of from about 5 μm to about 500 μm. More preferably, the support material can have a surface area in the range of from about 50 $m^2/g$ to about 500 $m^2/g$, pore volume of from about 0.5 cc/g to about 3.5 cc/g and average particle size of from about 10 μm to about 200 μm. The surface area can range from a low of about 50 $m^2/g$, 150 $m^2/g$, or 300 $m^2/g$ to a high of about 500 $m^2/g$, 700 $m^2/g$, or 900 $m^2/g$. The surface area also can range from a low of about 200 $m^2/g$, 300 $m^2/g$, or 400 $m^2/g$ to a high of about 600 $m^2/g$, 800 $m^2/g$, or 1,000 $m^2/g$. The average pore size of the support material can range of from about 10 Å to 1000 Å, about 50 Å to about 500 Å, about 75 Å to about 350 Å, about 50 Å to about 300 Å, or about 75 Å to about 120 Å.

In another embodiment, the support material can be one or more types of support materials which may or may not be treated differently. For example, one could use two different silicas each having different pore volumes or calcined at different temperatures. Likewise, one could use a silica that had been treated with a scavenger or other additive and a silica that had not.

The catalyst can convert light hydrocarbon alkenes to higher molecular weight oligomers at high temperatures and pressures. The light hydrocarbons or hydrocarbon feed stream can be or can include natural gas, natural gas liquids, or mixtures of both. The hydrocarbon feed stream can be derived directly from shale gas or other formations. The hydrocarbon feed stream can also originate from a refinery, such as from a fluid catalytic cracking (FCC) unit, coker, steam cracker, and pyrolysis gasoline (pygas) as well as alkane dehydrogenation processes, for example, ethane, propane and butane dehydrogenation.

The hydrocarbon feed stream can be or can include one or more olefins having from about 2 to about 12 carbon atoms. The hydrocarbon feed stream can be or can include one or more linear alpha olefins, such as ethene, propene, butenes, pentenes and/or hexenes. The process is especially applicable to ethene and propene oligomerization for making C4 to about C26 oligomers.

The hydrocarbon feed stream can contain greater than about 65 wt % olefins, such as greater than about 70 wt. % olefins or greater than about 75 wt % olefins. For example, the hydrocarbon feed stream can contain one or more C2 to C12 olefins in amounts ranging from a low of about 50 wt %, 60 wt % or 65 wt % to a high of about 70 wt %, 85 wt % or 100 wt %, based on the total weight of the feed stream. The hydrocarbon feed stream also can include up to 80 mol % alkanes, for example, methane, ethane, propane, butane, and pentane; although the alkane generally comprises less than about 50 mol % of the hydrocarbon feed stream, and preferably less than about 20 mol % of the hydrocarbon stream.

The hydrocarbon feed can have a temperature of 200° C. or higher. For example, the temperature of the hydrocarbon feed can range from a low of about 200° C., 300° C., or 350° C. to as high of about 500° C., 600° C., or 700° C. The temperature of the hydrocarbon feed also can be 200° C. or higher, 250° C. or higher, 300° C. or higher, 350° C. or higher, 380° C. or higher, 400° C. or higher, 425° C. or higher, 450° C. or higher, 460° C. or higher, 470° C. or higher, or 475° C. or higher, or 500° C. or higher.

The resulting oligomer(s) can be or can include one or more olefins having from 4 to 26 carbon atoms, such as 12 to 20 carbon atoms, or 16 to 20 carbon atoms. The resulting oligomers, for example, can include butene, hexene, octene, decene, dodecene, tetradecane, hexadecane, octadecene and eicosene and higher olefins, as well as any combinations thereof. The resulting oligomer(s) also can have less than about 5% aromatics and less than about 10 ppm sulfur. The resulting oligomer(s) also can have zero or substantially no aromatics and zero or substantially no sulfur.

The resulting oligomer(s) can be useful as precursors, feedstocks, monomers and/or comonomers for various commercial and industrial uses including polymers, plastics, rubbers, elastomers, as well as chemicals. For example, these resulting oligomer(s) are also useful for making polybutene-1, polyethylene, polypropylene, polyalpha olefins, block copolymers, detergents, alcohols, surfactants, oilfield chemicals, solvents, lubricants, plasticizers, alkyl amines, alkyl succinic anhydrides, waxes, and many other specialty chemicals.

The resulting oligomer(s) can be especially useful for production of diesel and jet fuels, or as a fuel additive. In certain embodiments, the resulting oligomer(s) can have a boiling point in the range of 170° C. to 360° C. and more particularly 200° C. to 300° C. The resulting oligomer(s) also can have a Cetane Index (CI) of 40 to 100 and more particularly 65 to 100. The resulting oligomer(s) also can have a pour point of −50° C. or −40° C.

As mentioned above, it has been surprisingly an unexpectedly discovered that the zinc-based catalysts and gallium-based catalysts described herein can oligomerize light alkene hydrocarbons to higher molecular weight oligomers at reaction temperatures never thought possible. Suitable reaction temperatures can exceed 200° C., such as about 400° C., about 450° C., about 500° C., about 525° C., about 550° C., and about 600° C. or higher. The reaction temperature, for example, can range from about 200° C. to about 600° C., about 350° C. to about 575° C., or about 350° C. to about 550° C. Of course, lower reaction temperatures are also possible, and can range for example a low of about 135° C., about 200° C. or about 225° C. to a high of about 350° C., about 400° C., or about 500° C.

Another significant advantage is that conventional oligomerization pressures can be used. For example, the reaction pressure can range from about 15 psig to about 4000 psig (1 Bar to 276 Bar), or about 15 psig to about 1500 psig (1 Bar to 103 Bar). The reaction pressure can also range from a low of about 15 psig (1 Bar), 500 psig (34.5 Bar) or 600 psig (41.4 Bar) to a high of about 1,000 psig (68.9 Bar), 1,200 psig (82.7 Bar), or 2,000 psig (138 Bar).

The oligomerization process can be carried out using any conventional technique. The process can be carried out, for example, in a continuous stirred tank reactor, batch reactor or plug flow reactor. One or more reactors operated in series or parallel can be used. The process can be operated at partial conversion to control the molecular weight of the product and unconverted olefins can be recycled for higher yields. Further, once the catalyst is deactivated with high molecular weight carbon, or coke, it can be regenerated using known techniques in the art, including for example, by combustion in air or nitrogen at a temperature of about 400° C. or higher.

EXAMPLES

The foregoing discussion can be further described with reference to the following non-limiting examples.

The Zn(II) and Ga(III) catalysts were prepared on a variety of supports using standard synthesis procedures including strong electrostatic adsorption (SEA), incipient wetness impregnation (IWI), and ion-exchange. Seven (7) catalysts were prepared with a range of weight loadings and in the presence of and absence of acid ($H^+$) sites. The catalyst formulations and procedures for making each catalyst follows below.

Catalyst 1: Zn(II) Supported on Beta Zeolite With Acid Sites (H-BEA)

Catalyst 1 was prepared by dissolving 6 g of zinc nitrate hexahydrate ($Zn(NO_3)_2$ $6H_2O$) in 20 mL of Millipore water followed by the addition of 5.00 g of H-BEA. This solution was then stirred for 45 minutes. The solid was separated from solution and washed three times using Millipore water. The obtained catalyst was dried for 16 hours at 125° C. and then calcined at 300° C. for 3 hours. The Zn loading as determined by Atomic Adsorption Spectroscopy (AAS) was approximately 1.5 wt % Zn.

Catalyst 2: Zn(II) Supported on Beta Zeolite Without Acid Sites (Na-BEA)

Catalyst 2 was prepared by suspending 15 g of H-BEA, the support precursor, in 50 mL of Millipore water. 11.33 g of sodium nitrate was dissolved in 100 mL of Millipore water and the resulting solution was added to the H-BEA suspension and stirred. The pH was adjusted to 7-7.5 using 0.1M NaOH solution. Within the first hour after pH of 7.5 is achieved, the pH rapidly dropped as $H^+$ ions were desorbed from the BEA framework and into the synthesis mixture. More NaOH solution was added to continuously to adjust the pH back to 7.5. Once the pH stabilized (after about 4 hours), the mixture was left to stir overnight at 80° C. to ensure a complete removal of $H^+$ ions.

After 24 hours, the suspension was washed for three to five times using Millipore water by centrifuging and decanting. The resulting zeolite support was then dried overnight at 125° C., before undergoing calcination at 250° C. for 3 hours, to obtain the Na-BEA support.

6 g of zinc nitrate hexahydrate ($Zn(NO_3)_2$ $6H_2O$) was dissolved in 20 mL of Millipore water. 5 g of Na-BEA was added to this solution and stirred for 45 minutes. The solid was separated from solution and washed three times using Millipore water. The catalyst was dried for 16 hours at 125° C. and then calcined at 300° C. for 3 hours. Then, 3.5 g of sodium nitrate ($Na(NO_3)$) was dissolved in 2 mL of water and impregnated on the Zn(II)/Na-BEA. The resulting catalysts was dried at 125° C. for 16 hours and then calcined at 300° C. for 3 hours. AAS was used to determine that the final catalyst contained approximately 1.1 wt % Zn.

Catalyst 3: Zn(II) Supported on Silica ($SiO_2$)

Catalyst 3 was prepared by synthesizing Zn(II) on SiO2 using pH-controlled strong electrostatic adsorption (SEA). A solution containing 2.5 g of zinc nitrate hexahydrate (Zn (NO3)2 6H2O) was made and the pH was adjusted to 11 using 30% ammonium hydroxide (NH4OH) solution, until a clear solution was obtained. NH4OH was added until all the precipitates were completely dissolved in solution. 10 g of Davasil silica was suspended 100 mL of Millipore water in a separate beaker and the pH was adjusted to 11 using NH4OH. The Zn solution was added rapidly to the SiO2 solution and stirred for 20 minutes. After the solid was settled, the solution was decanted, and the resulting slurry was washed with Millipore water and collected by vacuum filtration. The catalyst was dried for 16 hours at 125° C. and then calcined at 300° C. for 3 hours. AAS was used to determine that the final catalyst contained approximately 4.0 wt % Zn.

Catalyst 4: Ga(III) Supported on Beta Zeolite With Acid Sites (H-BEA)

Catalyst 4 was prepared by combining 0.55 g of gallium nitrate solution ($Ga(NO_3)_3$ xH2O) with a 1:1 molar equivalent amount of citric acid, dissolved in Millipore water. The solution was pH adjusted to 7 using sodium hydroxide (NaOH). The resulting solution was impregnated on 5.00 g of H-BEA support. The catalyst was dried at 125° C. for 16 hours and then calcined at 500° C. for 3 hours. AAS was used to determine that the final catalyst contained approximately 1.2 wt % Ga.

Catalyst 5: Ga(III) Supported on Beta Zeolite Without Acid Sites (Na-BEA)

Catalyst 5 was prepared by suspending 15 g of H-BEA, the support precursor, in 50 mL of Millipore water. 11.33 g of sodium nitrate was dissolved in 100 mL of Millipore water and the resulting solution was added to the H-BEA suspension and stirred. The pH was adjusted to 7-7.5 using 0.1M NaOH solution. Within the first hour after pH of 7.5 is achieved, the pH rapidly dropped as $H^+$ ions were desorbed from the BEA framework and into the synthesis mixture. More NaOH solution was added to continuously to adjust the pH back to 7.5. Once the pH stabilized (after about 4 hours), the mixture was left to stir overnight at 80° C. to ensure a complete removal of H+ ions.

After 24 hours, the suspension was washed for three to five times using Millipore water by centrifuging and decanting. The resulting zeolite support was then dried overnight at 125° C., before undergoing calcination at 250° C. for 3 hours, to obtain the Na-BEA support.

0.55 g of gallium nitrate solution ($Ga(NO_3)_3$ $xH_2O$) was combined with a 1:1 molar equivalent amount of citric acid, dissolved in Millipore water. The solution was pH adjusted to 7 using sodium hydroxide (NaOH). The resulting solution was impregnated on 5.00 g of Na-BEA support. The catalyst was dried at 125° C. for 16 hours and then calcined at 500° C. for 3 hours. AAS was used to determine that the final catalyst contained approximately 1.0 wt % Ga.

Catalyst 6: Ga(III) Supported on Silica ($SiO_2$)

Catalyst 6 was prepared by impregnating 10 g of Davasil silica with grade 636 (pore size=60 Å, surface area=480 $m^2/g$) with an aqueous solution containing 1.5 g of gallium nitrate solution ($Ga(NO_3)_3$ $xH_2O$) and 1.5 g of citric acid (Sigma Aldrich) dissolved in Millipore water. The catalyst was dried for 16 hours at 125° C. and then calcined at 500° C. for 3 hours. AAS was used to determine that the final catalyst contained approximately 2.7 wt % Ga.

Catalyst 7: Ga(III) Supported on Alumina ($Al_2O_3$)

Catalyst 7 was prepared by impregnating 10 g of alumina with an aqueous solution containing 1.5 g of gallium nitrate solution ($Ga(NO_3)_3$ $xH_2O$) and 1.5 g of citric acid (Sigma Aldrich) dissolved in Millipore water. The catalyst was dried for 16 hours at 125° C. and then calcined at 500° C. for 3 hours. AAS was used to determine that the final catalyst contained approximately 2.7 wt % Ga.

Oligomerization Tests

Example 1: Ethylene Feed at Atmospheric Pressure

Oligomerization tests were performed at atmospheric pressure in pure ethylene using a fixed bed reactor of ⅜-inch OD. In each test, the weight of the catalyst loaded into the reactor ranged from 0.5 g to 1 g. If less than 1 g, the catalyst was diluted with silica to reach a total of 1 g. The catalyst was treated in 50 ccm of $N_2$ while it ramped to the desired reaction temperature that varied between 200° C. and 500° C. The reaction was performed in 100% $C_2H_4$ using GHSVs ranging from 0.08 $s^{-1}$ to 0.38 $s^{-1}$. Products were sampled every 25 minutes and analyzed using a Hewlett Packard (HP) 6890 series gas chromatograph (GC) using a flame ionization detector (FID) with an Agilent HP-Al/S column (25 m in length, 0.32 mm ID, and 8 μm film thickness).

Figure 1B:
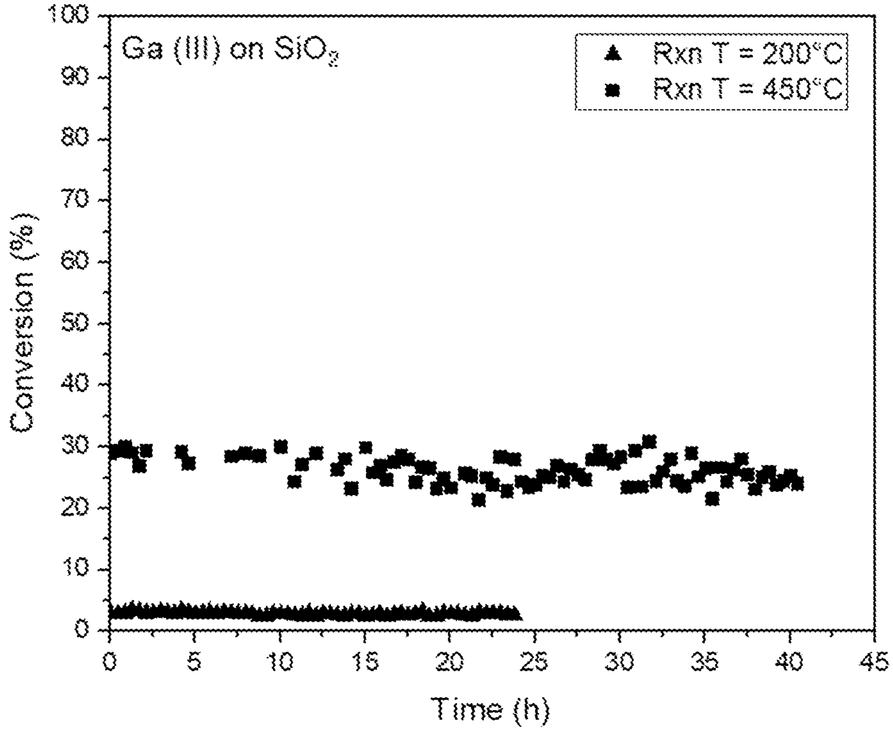
FIG. 1B shows the conversion (%) of supported Ga(III) on silica catalysts as a function of time in ethylene oligomerizations at 200° C. and 450° C.

FIG. 1A shows the conversion (%) of supported Zn(II) on silica catalysts as a function of time in ethylene oligomerizations at 200° C. and 450° C. FIG. 1B shows the conversion (%) of supported Ga(III) on silica catalysts as a function of time in ethylene oligomerizations at 200° C. and 450° C.

Figure 2A:
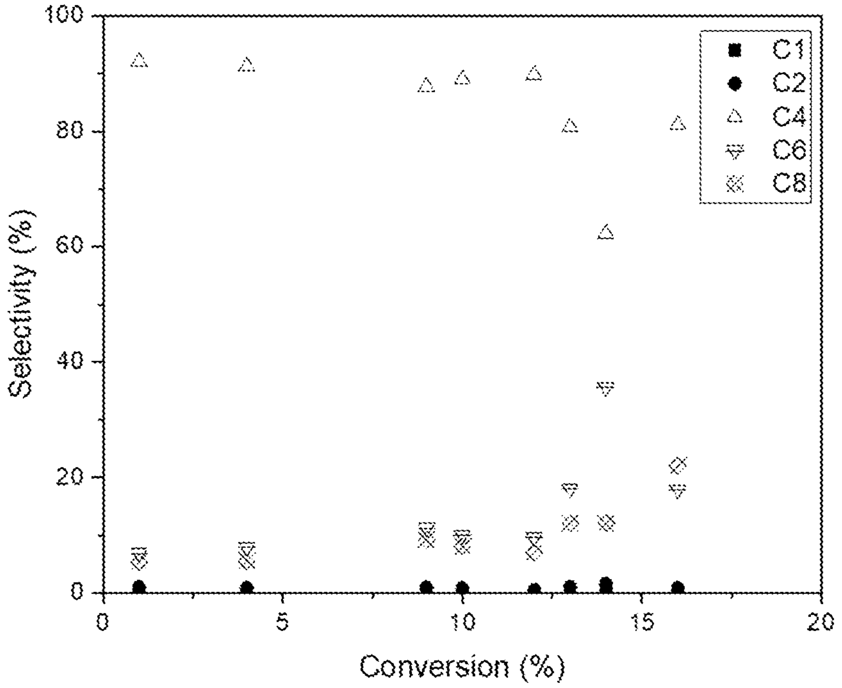
FIG. 2A shows the product distribution as a function of conversion for Ga(III) on $SiO_2$ at atmospheric pressure in pure ethylene at 250° C. The conversion was changed by varying the reactant flow rate.
Figure 2B:
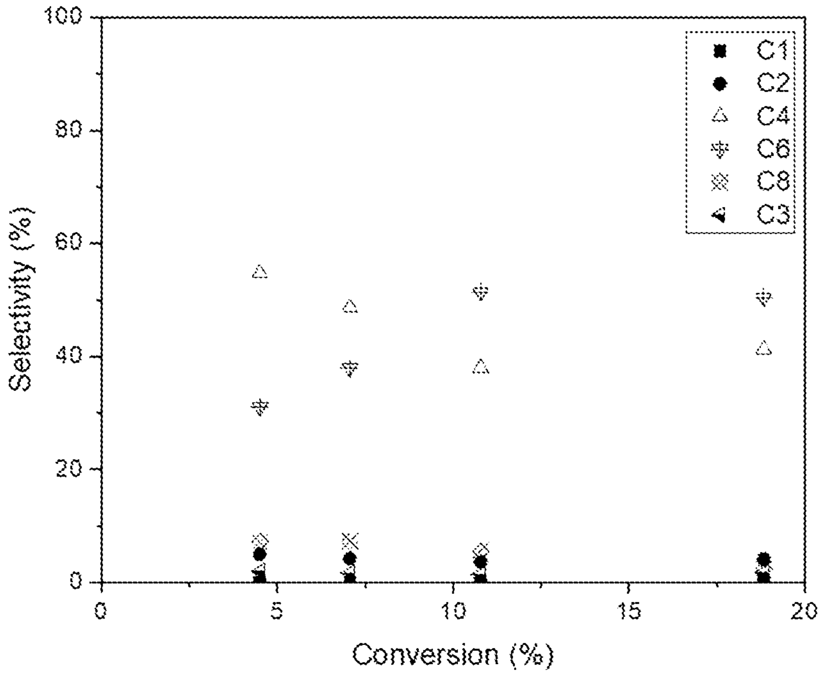
FIG. 2B shows the product distribution as a function of conversion for Ga(III) on $SiO_2$ at atmospheric pressure in pure ethylene at 450° C. The conversion was changed by varying the reactant flow rate.
Figure 3A:
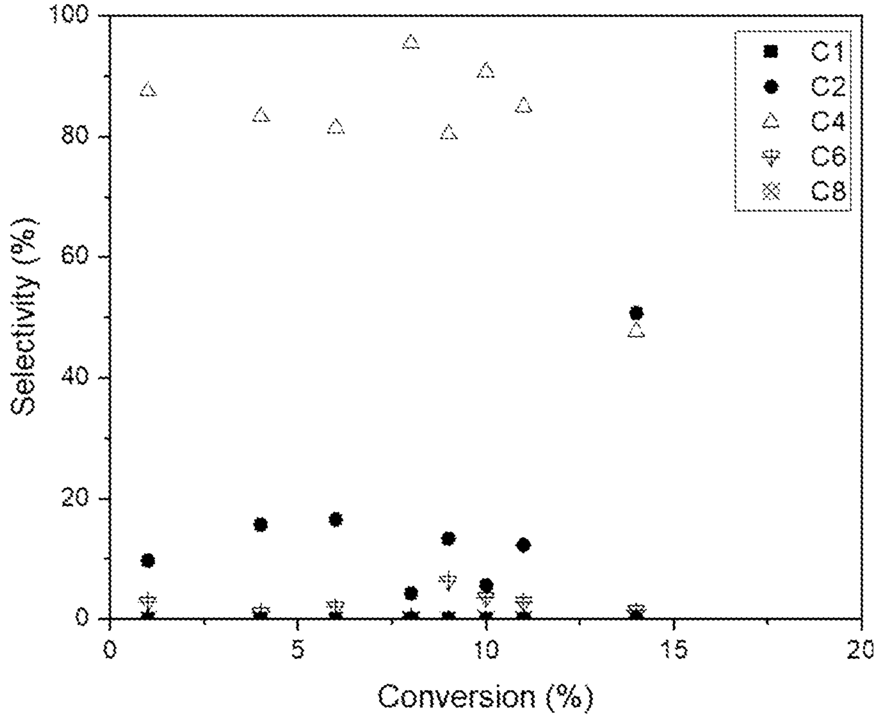
FIG. 3A shows the product distribution as a function of conversion for Zn(II) on $SiO_2$ at atmospheric pressure in pure ethylene at 250° C. The conversion was changed by varying the reactant flow rate.
Figure 3B:
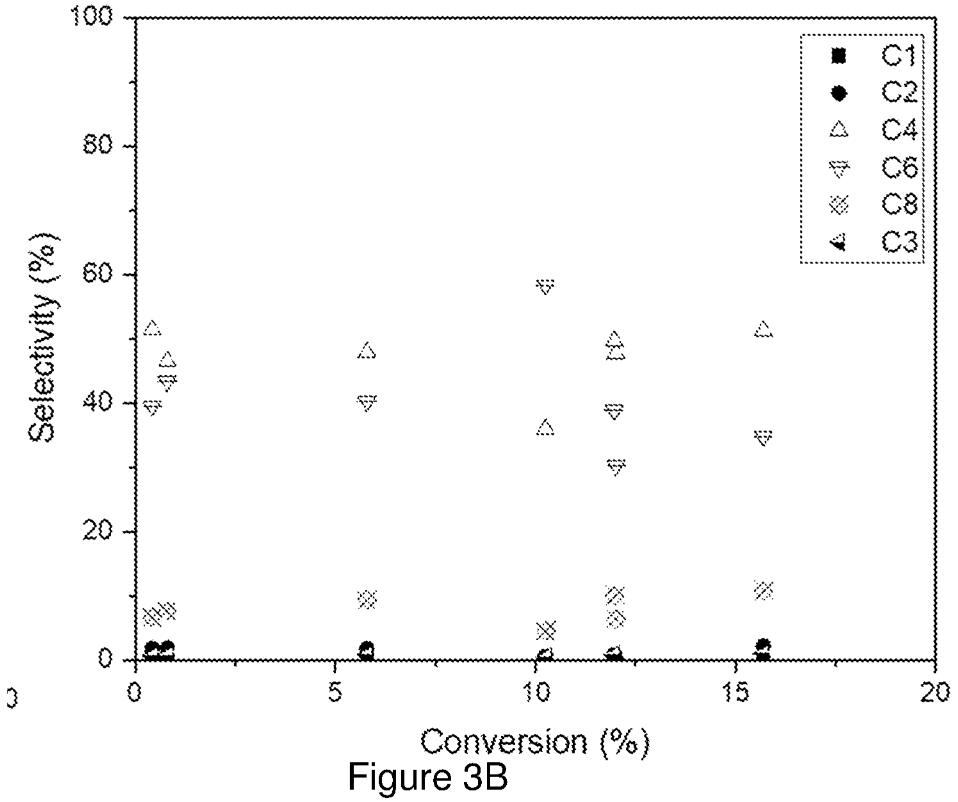
FIG. 3B shows the product distribution as a function of conversion for Zn(II) on $SiO_2$ at atmospheric pressure in pure ethylene at 450° C. The conversion was changed by varying the reactant flow rate.

FIGS. 2A-2B show the product distribution as a function of conversion for Ga(III) supported on $SiO_2$ (Catalyst 6) at atmospheric pressure in pure ethylene at different temperatures. FIGS. 3A to 3B show the product distribution as a function of conversion for Zn(II) on $SiO_2$ (Catalyst 3) at atmospheric pressure in pure ethylene at different temperatures.

Table 1 below summarizes the conversion and product distribution of ethylene oligomerization with Ga/$SiO_2$ (Catalyst 6). Table 2 shows the conversion and product distribution of ethylene oligomerization with Zn/$SiO_2$ (Catalyst 3). The conversion was changed by varying the reactant flow rate. The product selectivity was changed based on the reaction temperature and reactant feed. The conversion was changed by varying the reactant flow rate.

TABLE 1

Ethylene oligomerization results using Catalyst 6.

| P (psig) | T (° C.) | Conversion (%) | Molar Selectivity (%) $C_1$ | $C_2$ | $C_3$ | $C_4$ | $C_5$ | $C_6$ | $C_7$ | $C_8$ | $C_9$ |
|---|---|---|---|---|---|---|---|---|---|---|---|
| 5 | 250 | 1 | tr | 5 | — | 87 | — | 3 | — | 6 | — |
| 5 | 250 | 2 | tr | 3 | — | 85 | — | 4 | — | 8 | — |
| 5 | 250 | 5 | tr | 2 | — | 76 | — | 17 | — | 16 | — |
| 5 | 450 | 3 | 1 | 22 | 4 | 60 | — | 10 | — | 3 | — |
| 5 | 450 | 5 | 1 | 26 | 5 | 49 | — | 11 | — | 6 | — |
| 5 | 450 | 8 | 2 | 33 | 6 | 43 | — | 11 | — | 4 | — |
| 450 | 250 | 20 | tr | 1 | tr | 74 | — | 16 | — | 5 | — |

TABLE 2

Ethylene oligomerization results using Catalyst 3.

| P (psig) | T (° C.) | Conversion (%) | Molar Selectivity (%) $C_1$ | $C_2$ | $C_3$ | $C_4$ | $C_5$ | $C_6$ | $C_7$ | $C_8$ | $C_9$ |
|---|---|---|---|---|---|---|---|---|---|---|---|
| 5 | 250 | 1 | tr | 6 | — | 92 | — | 3 | — | 0 | — |
| 5 | 250 | 2 | tr | 12 | — | 87 | — | 1 | — | 0 | — |
| 5 | 250 | 5 | tr | 13 | — | 86 | — | 2 | — | 0 | — |
| 5 | 450 | 3 | 3 | 36 | 1 | 47 | — | 12 | — | 1 | — |
| 5 | 450 | 5 | 3 | 24 | 1 | 47 | — | 20 | — | 4 | — |
| 5 | 450 | 7 | 5 | 22 | 1 | 44 | — | 24 | — | 3 | — |
| 450 | 250 | 20 | tr | 1 | tr | 96 | — | — | — | — | — |

Under these conditions, 98-99% of the carbon feed was recovered as gas phase products and Zn(II) and Ga(III) were stable for up to 40 hours (not tested for longer times). As shown in Tables 1-2, higher reaction temperature lead to higher conversion and consequently a higher selectivity toward higher molecular weight products. As the conversion increased, the selectivity towards C4H8 decreased and the selectivity towards C6H12 increased, which is consistent with butenes being the primary product.

Ga(III) hydrogenation products (alkanes) were also obtained, even in the absence of H2 in the original feed. The selectivity towards ethane remained constant at about 1%. This suggests that H2 is being produced during the formation of other products, thus facilitating hydrogenation. While small amounts of alkanes are also produced on catalyst 3, the selectivity towards ethane (~5%) remained relatively constant as a function of conversion up to 20%. Additionally, $SiO_2$ catalysts were pretreated prior to exposure to C2H4 with 50 ccm of 5% H2/N2, and a slight increase in selectivity toward hydrogenation products was observed.

Figure 4A:
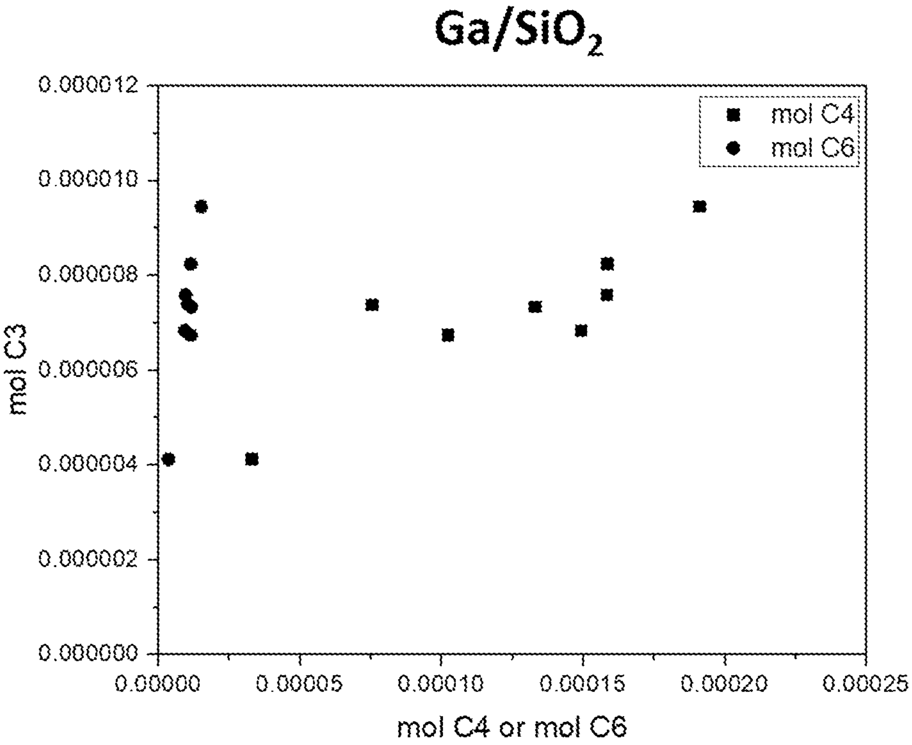
FIG. 4A shows the dependence of propylene produced relative to butene and hexene for Ga (III) on $SiO_2$.
Figure 4B:
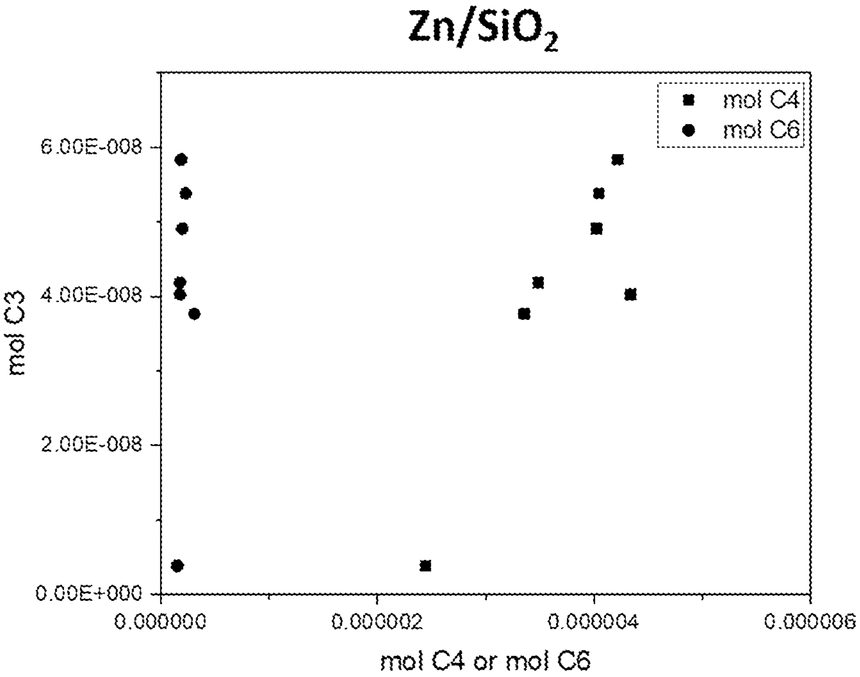
FIG. 4B shows the dependence of propylene produced relative to butene and hexene for Zn (II) on $SiO_2$.

Interestingly, when ethylene oligomerization was performed at 450° C., the formation of small amounts of propylene (~2%) was also observed. This was further investigated by comparing the propylene dependence on the formation of butenes and hexenes. FIG. 4A shows the dependence of propylene produced relative to butene and hexene for Ga (III) on $SiO_2$, and FIG. 4B shows the dependence of propylene produced relative to butene and hexene for Zn (II) on $SiO_2$. As depicted in FIGS. 4A and 4B, the undefined slope of the mol of propylene with respect to the mols of hexenes compared to the positive slope with respect to butenes suggests that the formation of propylene is directly related to the formation of butene. This may be the result of olefin metathesis (i.e. when ethylene and butene combine to form two propylene molecules).

These reactions with similar activity and product selectivity were also performed using Ga(III) on $Al_2O_3$ supported catalyst (Catalyst 7). Table 3 summarizes the conversions and products at low pressure, e.g., less than 1 atm.

TABLE 3

Catalyst performance for low pressure ethylene oligomerization using Catalyst 7.

| Reaction Conditions | Conversion (%) | $C_2$ Selectivity (%) | $C_3$ Selectivity (%) | $C_4$ Selectivity (%) | ($C_5$-$C_6$) Selectivity (%) | $C_{7+}$ Selectivity (%) |
|---|---|---|---|---|---|---|
| 250° C., 5 psig | 0.2 | 2.4 | 9 | 64.5 | 24.2 | — |
| 250° C., 5 psig | 1.2 | 4.4 | 1.1 | 32 | 10.2 | 52.4 |
| 400° C., 5 psig | 7.4 | 13 | 5 | 30 | 12.6 | 39.7 |

Example 2: Propylene Feed at Atmospheric Pressure

Oligomerization tests were performed on 1 g of catalyst at atmospheric pressure in pure propylene using a fixed bed reactor of ⅜-inch OD. The catalyst was treated in 50 ccm of N2 while it ramped to 200° C., reaction temperature. The reaction was performed in 100% C3H6 using GHSVs ranging from 0.08 s−1 to 0.38 s−1. Products were sampled every 25 minutes and analyzed using a Hewlett Packard (HP) 6890 Series gas chromatograph (GC) using a flame ionization detector (FID) with an Agilent HP-Al/S column (25 m in length, 0.32 mm ID, and 8 μm film thickness).

Figure 5A:
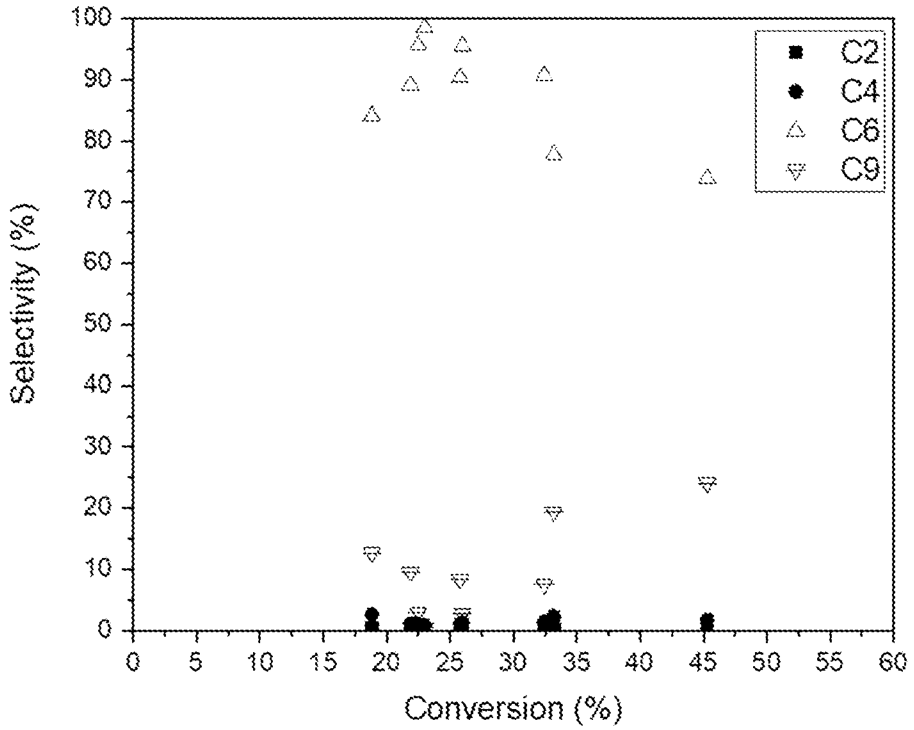
FIG. 5A shows the product distribution as a function of conversion for Ga(III) on $SiO_2$ at atmospheric pressure and 250° C. in pure propylene. The conversion was changed by varying the reactant flow rate.
Figure 5B:
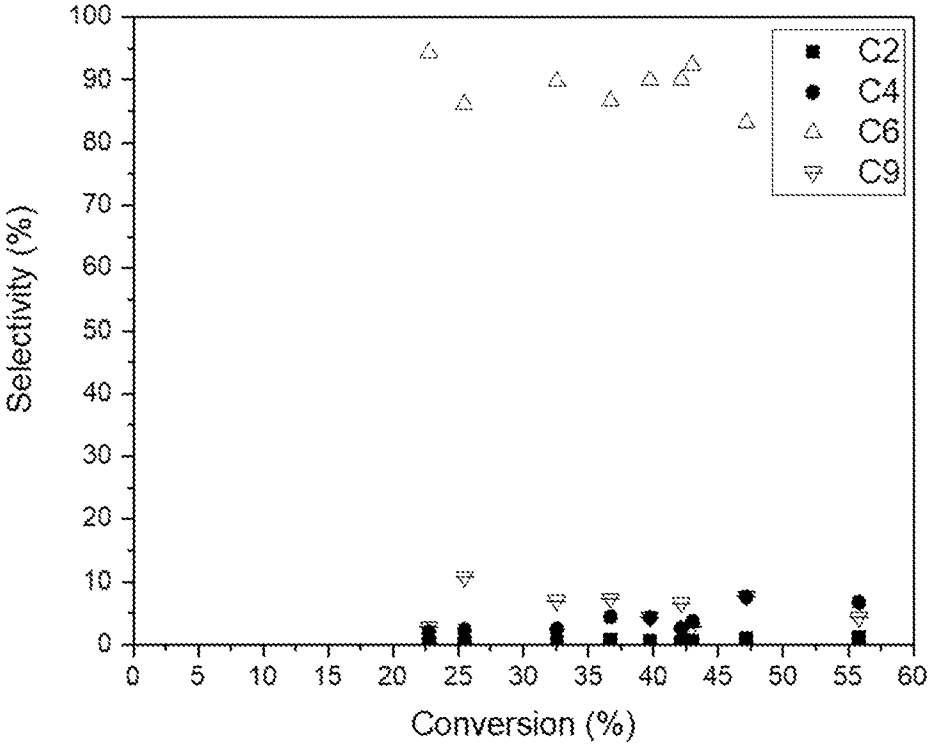
FIG. 5B shows the product distribution as a function of conversion for Ga(III) on $SiO_2$ at atmospheric pressure and 350° C. in pure propylene. The conversion was changed by varying the reactant flow rate.
Figure 5C:
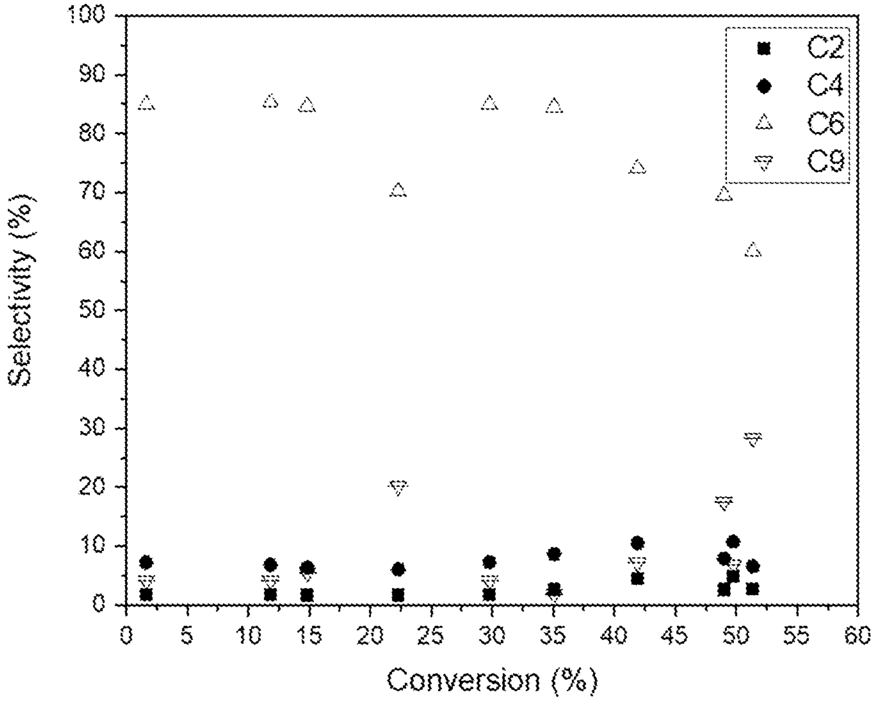
FIG. 5C shows the product distribution as a function of conversion for Ga(III) on $SiO_2$ at atmospheric pressure and 450° C. in pure propylene. The conversion was changed by varying the reactant flow rate.

C3H6 oligomerization produces C6H12+ C9H18+ . . . , but C2H4 and C4H8 are also formed. The reaction was performed in pure propylene at 250° C., 350° C., and 450° C. The product distributions for these reactions are shown for Ga(III) on SiO2 (Catalyst 6) in FIGS. 5A to 5C. FIG. 5A shows the product distribution as a function of conversion for Ga(III) on $SiO_2$ at atmospheric pressure and 250° C. in pure propylene. FIG. 5B shows the product distribution as a function of conversion for Ga(III) on $SiO_2$ at atmospheric pressure and 350° C. in pure propylene. FIG. 5C shows the product distribution as a function of conversion for Ga(III) on $SiO_2$ at atmospheric pressure and 450° C. in pure propylene. The conversions were changed by varying the reactant flow rate.

Figure 6A:
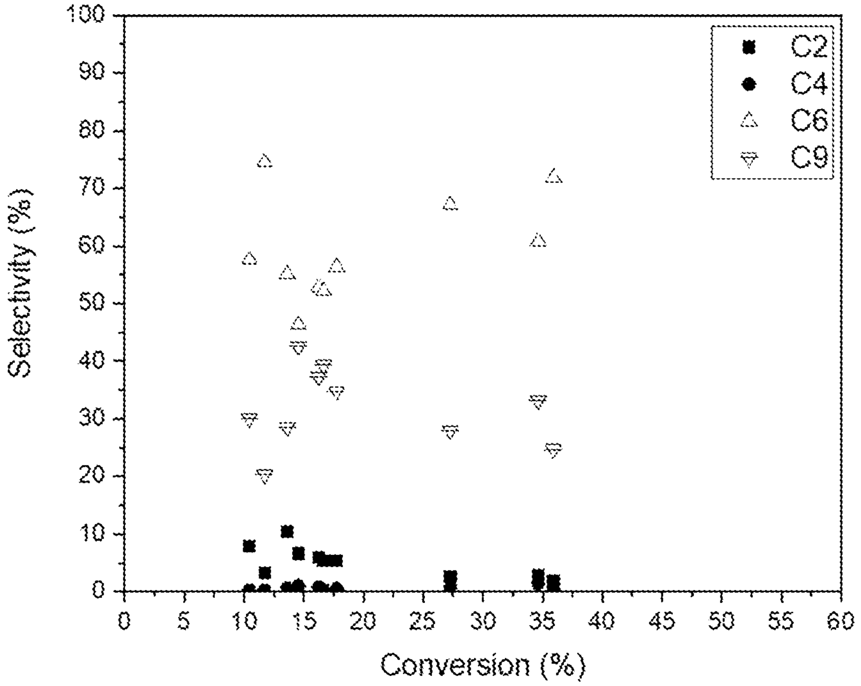
FIG. 6A shows the product distribution as a function of conversion for Zn(II) on $SiO_2$ at atmospheric pressure and 250° C. in pure propylene. The conversion was changed by varying the reactant flow rate.
Figure 6B:
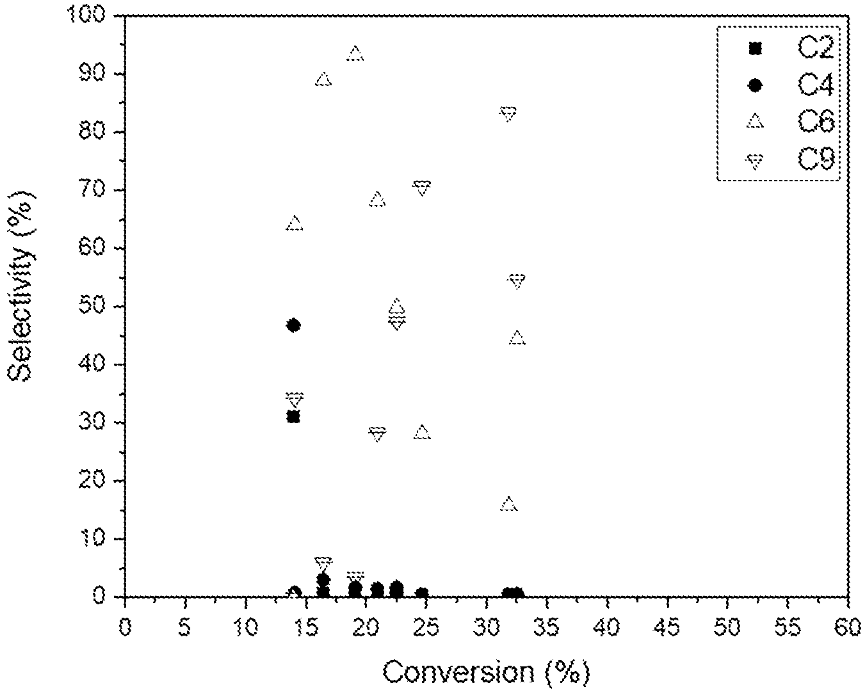
FIG. 6B shows the product distribution as a function of conversion for Zn(II) on $SiO_2$ at atmospheric pressure and 350° C. in pure propylene. The conversion was changed by varying the reactant flow rate.

The product distributions are shown for Zn(II) on $SiO_2$ (Catalyst 3) in FIGS. 6A and 6B. FIG. 6A shows the product distribution as a function of conversion for Zn(II) on $SiO_2$ at atmospheric pressure and 250° C. in pure propylene. The conversion was changed by varying the reactant flow rate. FIG. 6B shows the product distribution as a function of conversion for Zn(II) on $SiO_2$ at atmospheric pressure and 350° C. in pure propylene. The conversion was changed by varying the reactant flow rate.

Table 4 summarizes the conversion and product distribution of propylene oligomerization with Ga/SiO2 (Catalyst 6). Table 5 summarizes the conversion and product distribution of propylene oligomerization with Zn(II)/$SiO_2$ (Catalyst 3).

TABLE 4

Propylene oligomerization results using Catalyst 6.

| P | T | Conversion | Molar Selectivity (%) | | | | | | | | |
|---|---|---|---|---|---|---|---|---|---|---|---|
| (psig) | (° C.) | (%) | $C_1$ | $C_2$ | $C_3$ | $C_4$ | $C_5$ | $C_6$ | $C_7$ | $C_8$ | $C_9$ |
| 5 | 450 | 2 | 6.3 | 23.4 | 17.9 | 19.4 | — | 5.2 | — | — | 26.7 |
| 5 | 450 | 5 | 5.8 | 22.6 | 18.5 | 21.2 | — | 5.5 | — | — | 25.6 |
| 5 | 450 | 10 | 8.6 | 21 | 25.3 | 17.7 | — | 7.3 | — | — | 15.2 |
| 5 | 450 | 15 | 8.7 | 20.7 | 30.3 | 19.3 | — | 8.9 | — | — | 11.3 |
| 5 | 350 | 2 | 1.2 | 12.4 | 4.4 | 12.5 | — | 6.6 | — | — | 61.8 |
| 5 | 350 | 5 | 1.4 | 13 | 3.8 | 15 | — | 10.1 | — | — | 54.2 |
| 5 | 350 | 10 | 2.6 | 19.6 | 3.2 | 22.7 | — | 14.9 | — | — | 35.9 |
| 5 | 350 | 12 | 2.9 | 19.2 | 5.8 | 25.4 | — | 14.7 | — | — | 31 |
| 5 | 250 | 1 | 0.1 | 5.5 | 3.9 | 6.3 | — | 8.9 | — | — | 75.1 |
| 5 | 250 | 3 | 0.1 | 5.9 | 6.3 | 6.7 | — | 7.8 | — | — | 71.9 |
| 5 | 250 | 5 | 0.2 | 7.4 | 5.3 | 7.4 | — | 16.1 | — | — | 52.3 |
| 5 | 250 | 8 | 0.2 | 10.4 | 7.7 | 8.9 | — | 23.5 | — | — | 43.4 |

TABLE 5

Propylene oligomerization results using Catalyst 3.

| P | T | Conversion | Molar Selectivity (%) | | | | | | | | |
|---|---|---|---|---|---|---|---|---|---|---|---|
| (psig) | (° C.) | (%) | $C_1$ | $C_2$ | $C_3$ | $C_4$ | $C_5$ | $C_6$ | $C_7$ | $C_8$ | $C_9$ |
| 5 | 450 | 2 | 7.4 | 19.7 | 29.7 | 19.4 | — | 12 | — | — | 11.8 |
| 5 | 450 | 5 | 8.4 | 21 | 24.1 | 18.7 | — | 22.6 | — | — | 5.2 |
| 5 | 450 | 10 | 13.5 | 14.9 | 27.9 | 17.1 | — | 23.5 | — | — | 3.1 |
| 5 | 450 | 15 | 7.2 | 16.7 | 25 | 16.6 | — | 27.1 | — | — | 7.4 |
| 5 | 350 | 2 | 4.5 | 25.5 | 6 | 21 | — | 13 | — | — | 30 |
| 5 | 350 | 5 | 1.2 | 26 | 6 | 26.1 | — | 13 | — | — | 20.2 |
| 5 | 350 | 10 | 0.8 | 23.7 | 4.6 | 24.6 | — | 15.6 | — | — | 23.6 |
| 5 | 350 | 12 | 1.2 | 17 | 4.9 | 16.7 | — | 29.1 | — | — | 22.2 |
| 5 | 250 | 1 | 0 | 3.8 | 9.2 | 3.2 | — | 50.5 | — | — | 28.1 |
| 5 | 250 | 3 | 0 | 2 | 6.1 | 1.3 | — | 52.2 | — | — | 29.6 |
| 5 | 250 | 5 | 0 | 5.9 | 8.9 | 5.4 | — | 36.7 | — | — | 30.8 |
| 5 | 250 | 8 | 0 | 6.2 | 6.2 | 6.6 | — | 41.4 | — | — | 30 |

Figure 7A:
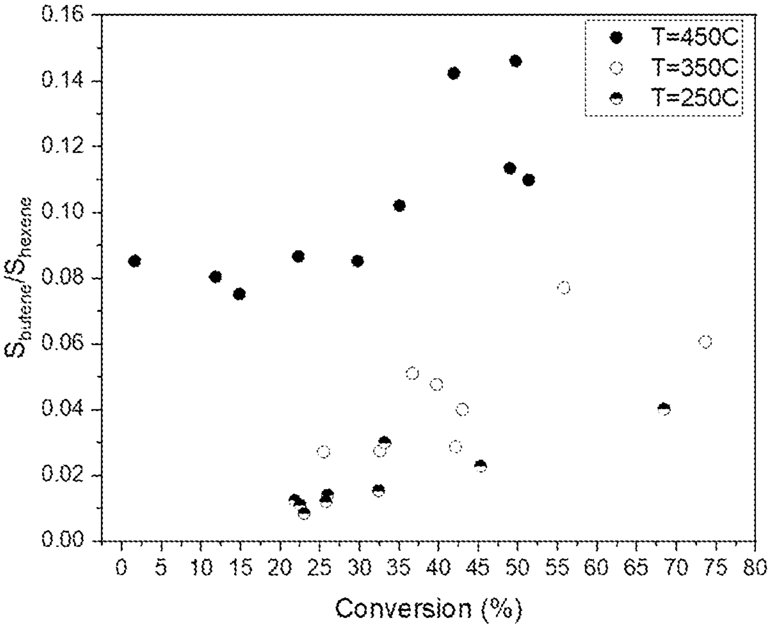
FIG. 7A shows the ratio of selectivity for butene/hexene as a function of conversion for each temperature for Ga(III) on $SiO_2$.
Figure 7B:
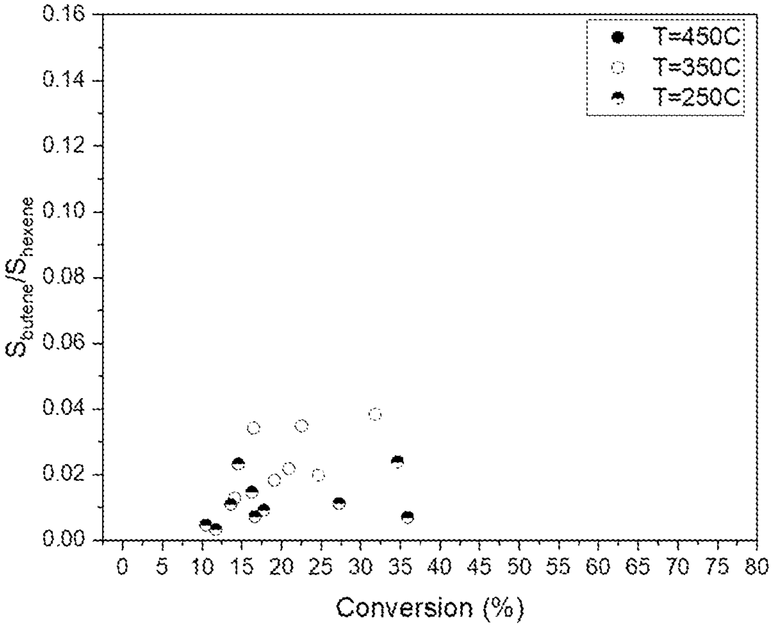
FIG. 7B shows the ratio of selectivity for butene/hexene as a function of conversion for each temperature for Zn(II) on $SiO_2$.

FIGS. 7A-B shows the ratio of selectivity to butene/hexene as a function of conversion for each temperature. FIG. 7A shows the ratio of selectivity for butene/hexene as a function of conversion for each temperature for Ga(III) on $SiO_2$, and FIG. 7B shows the ratio of selectivity for butene/hexene as a function of conversion for each temperature for Zn(II) on $SiO_2$. This ratio remained relatively constant, indicating that the rate of metathesis to oligomerization was independent of temperature. Interestingly, butene and ethylene were formed while typical oligomerization products were produced at all temperatures. This demonstrates the reverse of what was observed in the ethylene reactions of Example 1, suggesting that propylene was activated more easily than ethylene so higher conversions were observed in the propylene feed. In any event, higher temperatures lead to a higher conversion.

Example 3: Ethylene Feed at High Pressure

High pressure reactor tests were performed in a stainless-steel reactor tube of ½-inch OD. The weight of the catalyst loaded into the reactor ranged from 250 mg to 500 mg and was diluted to 1 g using silica. Once the reactor was sealed and leak tested, it was pressurized, with values ranging from 100 psig and 300 psig. The catalyst was treated in 50 ccm of N2 while it ramped to the desired reaction temperature, which ranged from 200° C. to 500° C. The reaction was performed in 100% C2H4 using GHSVs ranging from 0.02 s−1 to 0.11 s−1. Products were sampled every 22 minutes and analyzed using a Hewlett Packard (HP) 7890 Series gas chromatograph (GC) using a flame ionization detector (FID) with an Agilent HP-1 column (60 m in length, 0.32 mm ID, and 0.5 μm film thickness) respectively.

Ga(III) supported on beta zeolite without acid sites (Na-BEA) (Catalyst 5) was tested at 17 atm pressure of ethylene and with a flow rate of 50 ccm 100% ethylene between 200° C. and 500° C. for olefin oligomerization. Above 400° C., there were high (>50%) ethylene conversions. A higher selectivity for butene (C4=) was observed at very low conversions of less than 2%. Surprisingly, a significant amount of propylene (C3=) was formed at conversions greater than 10%, as depicted in FIG. 8, which shows ethylene conversion at varying temperature of 200° C. to 550° C. at 17 atm pressure on Ga (III) on Na-BEA.

The high selectivity towards C3= was unexpected as oligomerization of ethylene should only produce even-carbon-numbered hydrocarbons. At temperatures near 500° C., the conversion was very high, e.g., greater than 90%. Small amounts of alkanes were also observed. Ethylene oligomerization over Zn (II) on Na-BEA exhibited identical observations to the experiment with Ga (III) on Na-BEA.

Figure 8:
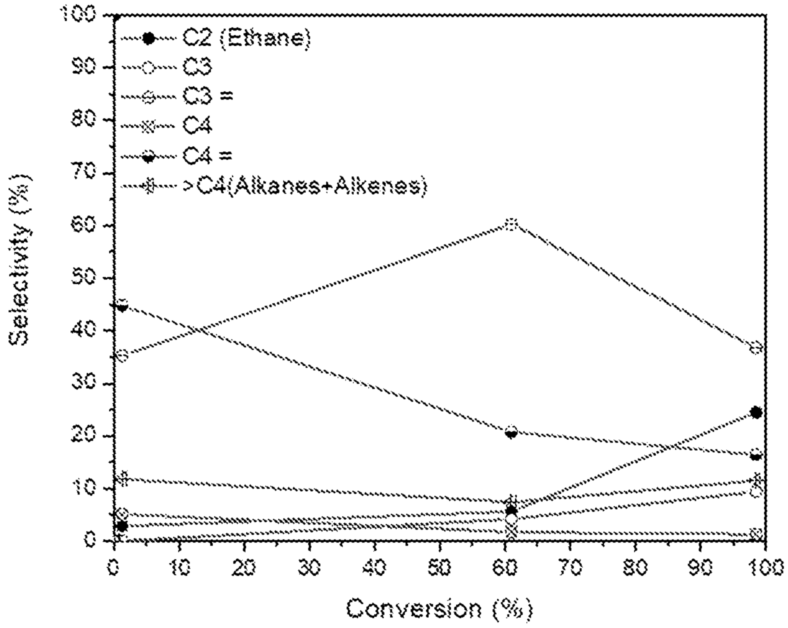
FIG. 8 shows ethylene conversion at varying temperature of 200° C. to 550° C. at 17 atm pressure on Ga (III) on Na-BEA.

FIG. 8 shows the C2H4 conversion in the oligomerization was changed by varying the temperature from at 200° C. to 550° C. at 17 atm pressure on Ga (III) on Na-BEA and products are categorized by their carbon number. Conversions greater than 50% resulted in higher molecular weight products that were condensed as a liquid and were analyzed offline at the end of reaction using mass spectrometry (GC-MS) to identify the composition of the liquid phase products. These liquid phase products showed signs of varying hydrocarbons up to C18 hydrocarbons (higher molecular weight products likely did not come off the GC column), including paraffins, olefins, and saturated rings, however, there was little evidence of branched hydrocarbons.

X-Ray Absorption Data

To elucidate the structures of the Zn(II) and Ga(III) catalysts, catalyst samples 1 to 6 were examined on the advanced photon source (APS) beamline facility at Argonne national lab (ANL). Spectroscopic data collection for X-ray Absorption Spectroscopy (XAS), an element specific technique, which contains Extended X-ray Absorption Fine Structure (EXAFS) and X-ray Absorption Near-Edge Structure (XANES) was carried out at ambient and pretreatment conditions. The catalyst samples (~20 mg) were pressed into a cylindrical sample holder consisting of six wells, forming a self-supporting wafer to prepare for this test.

The catalyst structure prior to pretreatment or reaction conditions was obtained by first dehydrating the catalysts at 500° C. in He. When comparing the XANES of the catalysts to references of known oxidation states, it was shown that the Zn catalyst has the Zn2+ oxidation state and the Ga catalyst has the Ga3+ oxidation state. Ga(III) and Zn(II) were formed respectively and each contained about four M-O bonds, independent of the type of support.

Figure 9A:
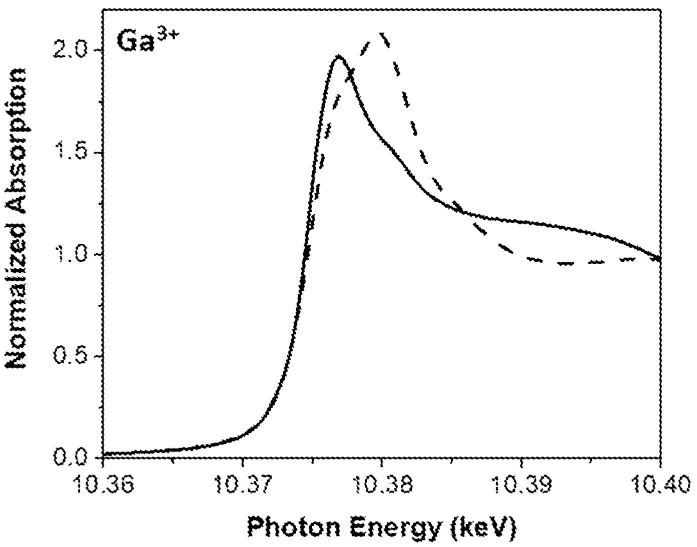
FIG. 9A shows XANES data for Ga(III) catalyst on $SiO_2$ (solid) compared to $Ga_2O_3$ (dash) after dehydration at 500° C. in He.
Figure 9B:
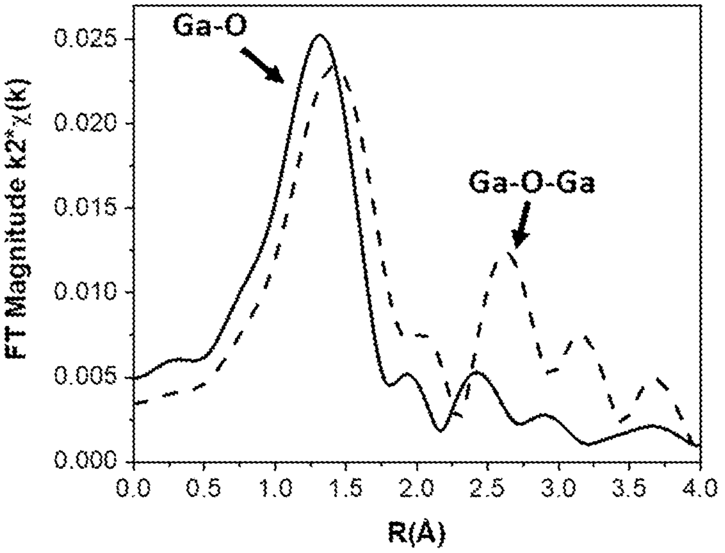
FIG. 9B shows EXAFS data for Ga(III) catalyst on $SiO_2$ (solid) compared to $Ga_2O_3$ (dash) after dehydration at 500° C. in He.

FIG. 9A shows XANES data for Ga(III) catalyst on $SiO_2$ (solid) compared to $Ga_2O_3$ (dash) after dehydration at 500° C. in He. FIG. 9B shows EXAFS data for Ga(III) catalyst on $SiO_2$ (solid) compared to $Ga_2O_3$ (dash) after dehydration at 500° C. in He.

Figure 10A:
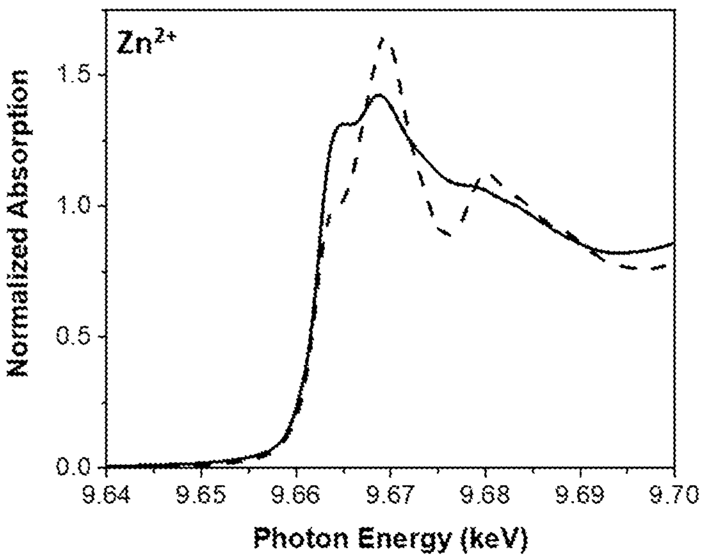
FIG. 10A shows XANES data for Zn(II) catalyst on $SiO_2$ (solid) compared to ZnO (dash) after dehydration at 500° C. in He.
Figure 10B:
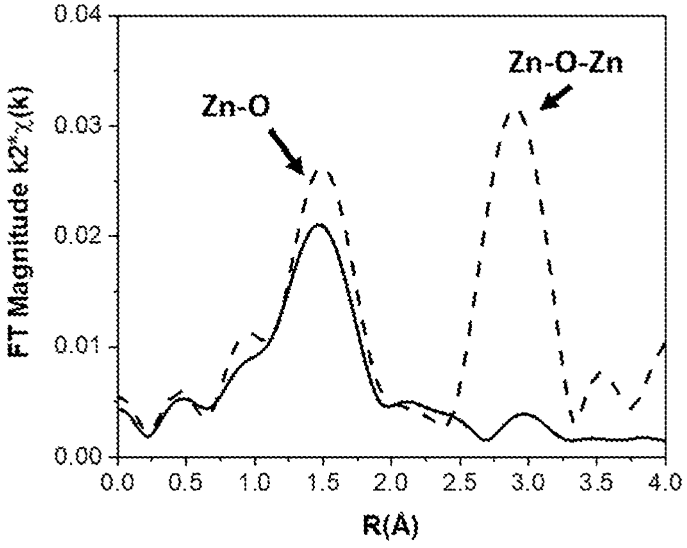
FIG. 10B shows XANES data for Zn(II) catalyst on $SiO_2$ (solid) compared to ZnO (dash) after dehydration at 500° C. in He.

FIG. 10A shows XANES data for Zn(II) catalyst on $SiO_2$ (solid) compared to ZnO (dash) after dehydration at 500° C. in He. FIG. 10B shows XANES data for Zn(II) catalyst on $SiO_2$ (solid) compared to ZnO (dash) after dehydration at 500° C. in He.

Figure 11A:
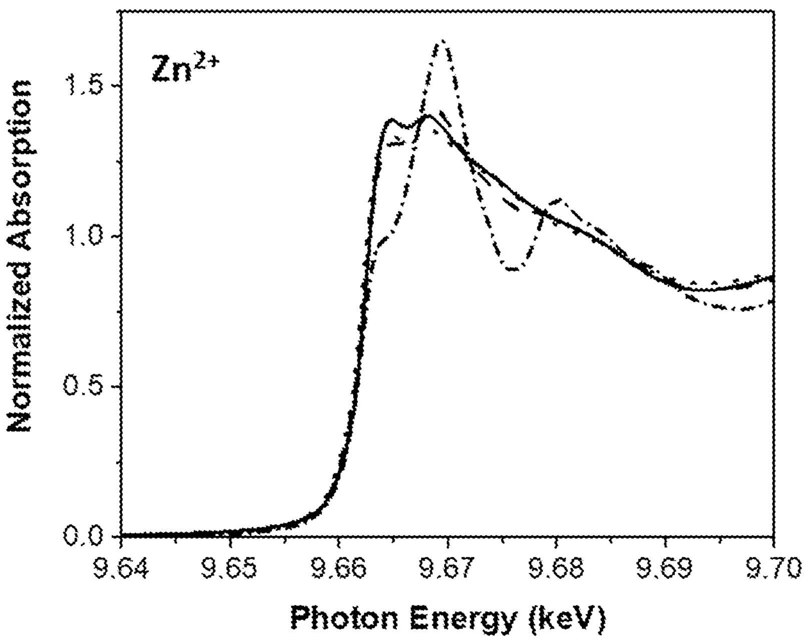
FIG. 11A shows XANES for Zn (II) on $SiO_2$ 1) dehydration at 500° C. (solid) and $H_2$ exposure at 2) 200° C. (dash) and 3) 550° C. (dot) compared to the bulk metal oxide (dash-dot).
Figure 11B:
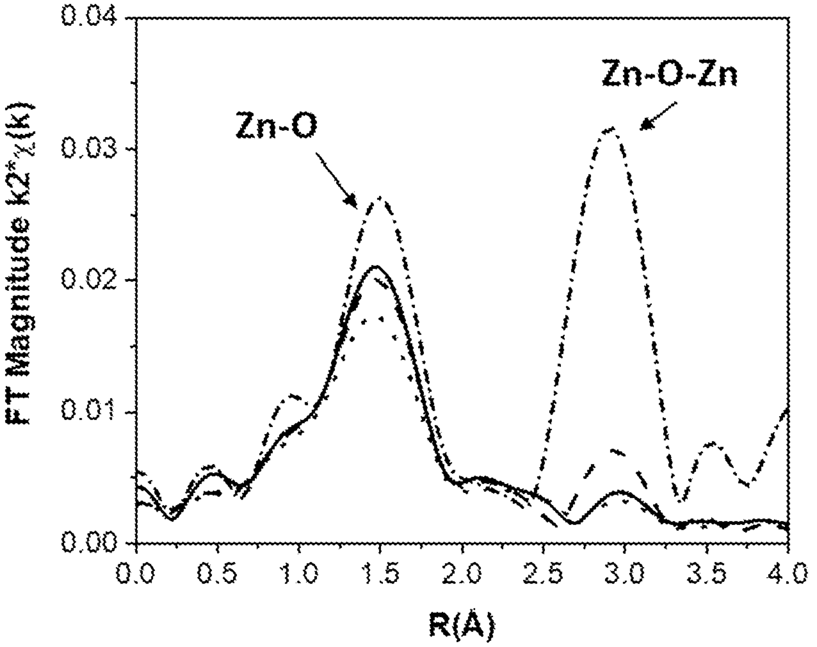
FIG. 11B shows EXAFS for Zn (II) on $SiO_2$ 1) dehydration at 500° C. (solid) and $H_2$ exposure at 2) 200° C. (dash) and 3) 550° C. (dot) compared to the bulk metal oxide (dash-dot).
Figure 12A:
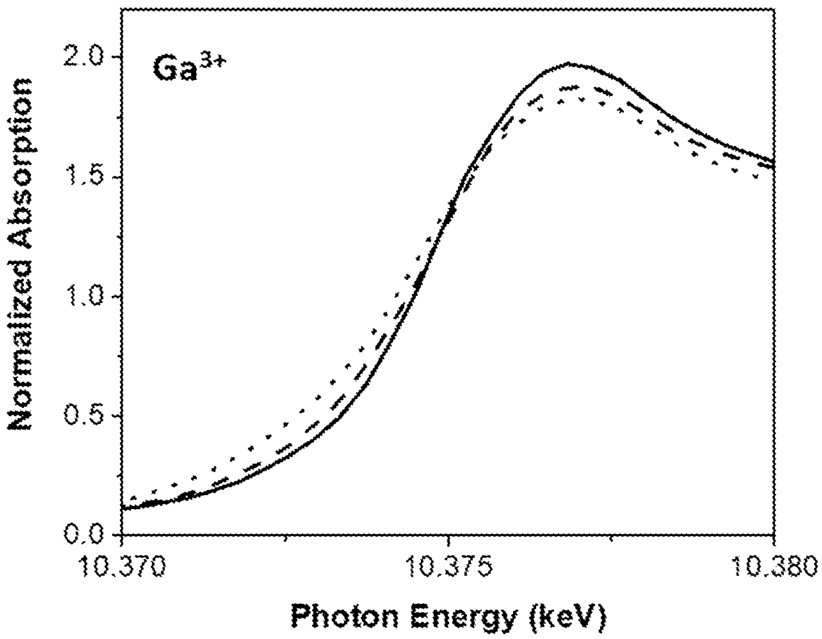
FIG. 12A shows. XANES for Ga (III) on $SiO_2$ 1) dehydration at 500° C. (solid) and $H_2$ exposure at 2) 200° C. (dash) and 3) 550° C. (dot).
Figure 12B:
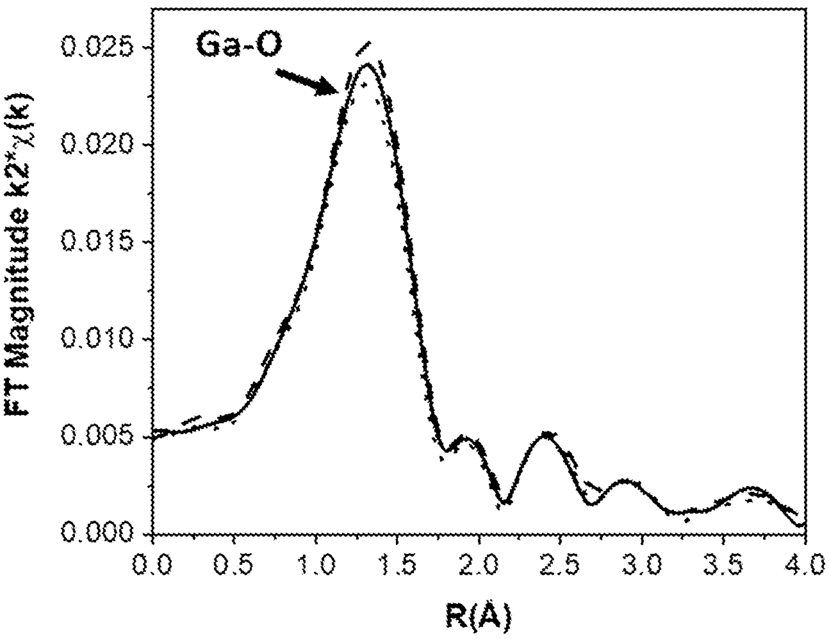
FIG. 12B shows EXAFS for Ga (III) on $SiO_2$ 1) dehydration at 500° C. (solid) and $H_2$ exposure at 2) 200° C. (dash) and 3) 550° C. (dot).

The in-situ structure for these catalysts was studied by treating them in H2 at increasing temperatures, and while the Zn2+ and Ga3+ oxidation states were maintained, slight changes in catalyst structure were observed. FIG. 11A shows XANES for Zn (II) on $SiO_2$ 1) dehydration at 500° C. (solid) and $H_2$ exposure at 2) 200° C. (dash) and 3) 550° C. (dot) compared to the bulk metal oxide (dash-dot). FIG. 11B shows EXAFS for Zn (II) on $SiO_2$ 1) dehydration at 500° C. (solid) and $H_2$ exposure at 2) 200° C. (dash) and 3) 550° C. (dot) compared to the bulk metal oxide (dash-dot). FIG. 12A shows. XANES for Ga (III) on $SiO_2$ 1) dehydration at 500° C. (solid) and $H_2$ exposure at 2) 200° C. (dash) and 3) 550° C. (dot). FIG. 12B shows EXAFS for Ga (III) on $SiO_2$ 1) dehydration at 500° C. (solid) and $H_2$ exposure at 2) 200° C. (dash) and 3) 550° C. (dot).

In the case of Zn (II) on $SiO_2$ (FIG. 11A), $H_2$ treatment at increasing temperatures led to the XANES energy, or the inflection point in the curve, to remain unchanged at 9.6625 keV. The shape of the white line, or the first feature past the XANES energy exhibited subtle changes in peak ratios, i.e., the intensity of the first peak increased relative to the second peak with higher temperatures in $H_2$. The EXAFS shows that the FT mag intensity decreased with increasing temperature in $H_2$, consistent with a loss of Zn—O bonds.

In the case of Ga (III) on $SiO_2$ (FIG. 12A), $H_2$ treatment at increasing temperatures led to the XANES energy, or the inflection point in the curve, to remain unchanged at 10.3750 keV. The intensity of the white line, or the first feature past the XANES energy, decreased, and the growth of a pre-edge feature occurred with higher temperatures in $H_2$. The EXAFS shows that the FT mag intensity slightly decreased with increasing temperature in $H_2$, consistent with a loss of Ga—O bonds.

When the samples were treated in $H_2$, there was a partial loss of metal-support oxygen bonds, presumably due to the formation of metal-hydrogen bonds. A lack of second nearest metal neighbors is consistent with the single site structure being maintained, even in the presence of $H_2$ at high temperature. The combined XANES and EXAFS suggests the formation of small amounts of metal hydrides. The overall geometry of both catalysts is expected to be maintained when the hydride intermediate is formed, so that Ga and Zn will likely remain 4 coordinated. It is thought that metal-oxygen bonds are lost to the formation of metal-hydrogen bonds, which provides indirect evidence of the metal hydride intermediate. Metal-hydrogen scattering cannot be detected directly by XAS because H is a light scatterer.

Figure 13A:
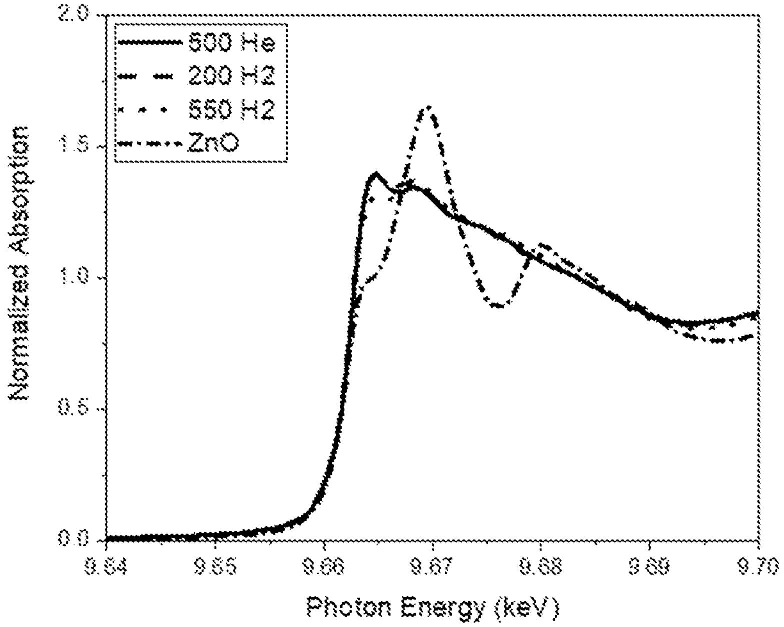
FIG. 13A shows XANES for Zn (II) on Na-BEA 1) dehydration at 500° C. (solid) and $H_2$ exposure at 2) 200° C. (dash) and 3) 550° C. (dot) compared to the bulk metal oxide (dash-dot).

Similar results were obtained for the Zn and Ga counterparts on zeolite materials. FIG. 13A shows XANES for Zn (II) on Na-BEA 1) dehydration at 500° C. (solid) and $H_2$ exposure at 2) 200° C. (dash) and 3) 550° C. (dot) compared to the bulk metal oxide (dash-dot).

Figure 13B:
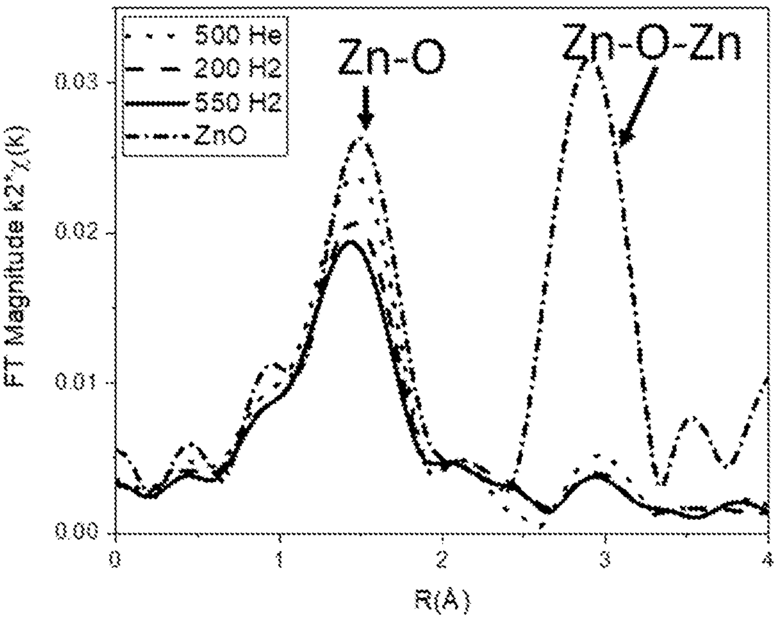
FIG. 13B shows EXAFS for Zn (II) on Na-BEA 1) dehydration at 500° C. (solid) and $H_2$ exposure at 2) 200° C. (dash) and 3) 550° C. (dot) compared to the bulk metal oxide (dash-dot).
Figure 14A:
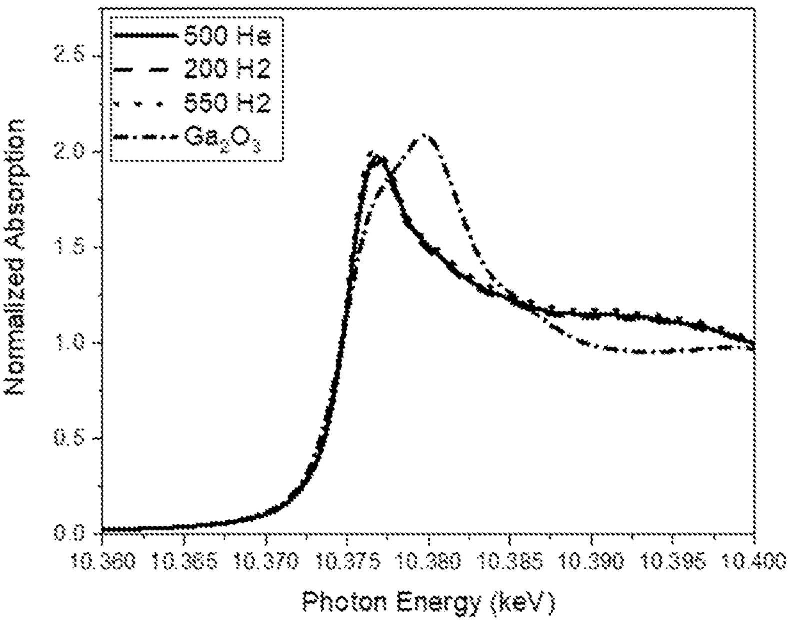
FIG. 14A shows XANES for Ga (III) on Na-BEA 1) dehydration at 500° C. (solid) and $H_2$ exposure at 2) 200° C. (dash) and 3) 550° C. (dot) compared to the bulk metal oxide (dash-dot).
Figure 14B:
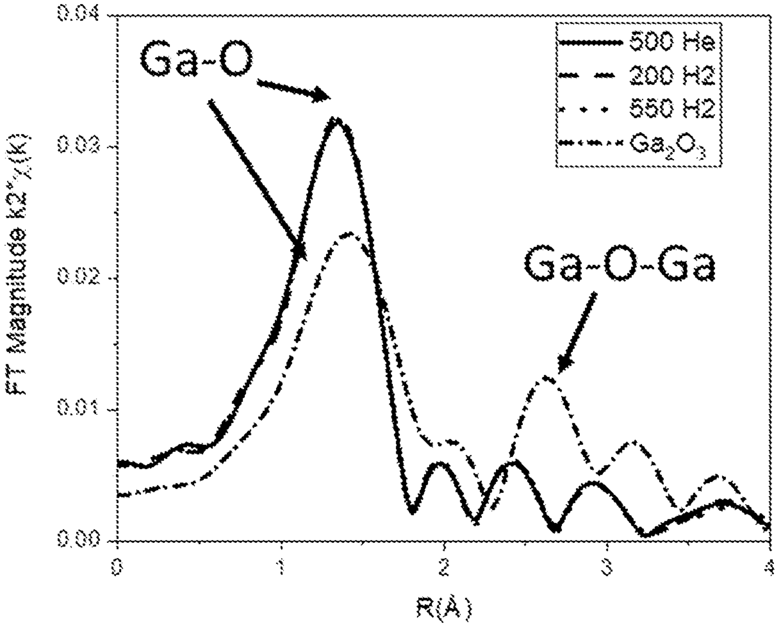
FIG. 14B shows EXAFS for Ga (III) on Na-BEA 1) dehydration at 500° C. (solid) and $H_2$ exposure at 2) 200° C. (dash) and 3) 550° C. (dot) compared to the bulk metal oxide (dash-dot).

FIG. 13B shows EXAFS for Zn (II) on Na-BEA 1) dehydration at 500° C. (solid) and H2 exposure at 2) 200° C. (dash) and 3) 550° C. (dot) compared to the bulk metal oxide (dash-dot). FIG. 14A shows XANES for Ga (III) on Na-BEA 1) dehydration at 500° C. (solid) and $H_2$ exposure at 2) 200° C. (dash) and 3) 550° C. (dot) compared to the bulk metal oxide (dash-dot). FIG. 14B shows EXAFS for Ga (III) on Na-BEA 1) dehydration at 500° C. (solid) and $H_2$ exposure at 2) 200° C. (dash) and 3) 550° C. (dot) compared to the bulk metal oxide (dash-dot).

To further evaluate the metal-support oxygen bonds, certain catalyst samples were dehydrated in inert (He) at 500° C., cooled to room temperature and then sealed in He. Subsequent treatments in pure $H_2$ at 200° C. and 550° C. were performed, and X-ray absorption data were collected under a pure hydrogen atmosphere at room temperature.

Table 6 shows the metal-oxygen fitting parameters for the scanned catalyst samples and treatments. As shown in Table 6, the pre-reaction structure was a four coordinate metal on a support. Increasing the temperature in hydrogen lead to the loss of more metal-oxygen bonds, which can be interpreted as the formation of small amounts of metal hydrides, which are known to facilitate oligomerization.

TABLE 6

Fitting parameters of M—O bonds.

| Sample | Pretreatment Conditions | XANES Energy (keV) | Scattering Path | CN | R (Å) | $\Delta\sigma^2$ (Å$^2$) | $\Delta E_o$ (eV) |
|---|---|---|---|---|---|---|---|
| $Ga_2O_3$ | Air, 35° C. | 10.3751 | Ga—O | 6.0 | 2.00 | | |
| (Comparative) | | | | 4.0 | 1.83 | | |
| Ga (III) on $SiO_2$ | He 500° C. | 10.3750 | Ga—O | 4.0 | 1.80 | 0.005 | −2.9 |
| (Catalyst 6) | $H_2$ 200° C. | 10.3749 | Ga—O | 3.8 | 1.80 | 0.005 | −3.0 |
| | $H_2$ 550° C. | 10.3747 | Ga—O | 3.7 | 1.80 | 0.005 | −2.9 |
| Ga (III) on | He 500° C. | 10.375 | Ga—O | 4.0 | 1.81 | 0.005 | −3.1 |
| Zeolite | $H_2$ 200° C. | 10.375 | Ga—O | 4.0 | 1.81 | 0.005 | −1.8 |
| (Catalyst 5) | $H_2$ 550° C. | 10.375 | Ga—O | 4.0 | 1.81 | 0.005 | −2.5 |
| Ga (III) on $Al_2O_3$ | He 500° C. | 10.3751 | Ga—O | 3.9 | 1.84 | −1.0 | 0.2 |
| (Catalyst 7) | | | | | | | |
| ZnO | Air, 35° C. | 9.6625 | Zn—O | 4.0 | 1.98 | | |
| (Comparative) | | | | | | | |
| Zn (II) on $SiO_2$ | He 500° C. | 9.6625 | Zn—O | 4.0 | 1.95 | 0.005 | −0.4 |
| (Catalyst 3) | $H_2$ 200° C. | 9.6625 | Zn—O | 3.9 | 1.95 | 0.005 | −0.8 |
| | $H_2$ 550° C. | 9.6623 | Zn—O | 3.5 | 1.94 | 0.005 | 0.4 |
| Zn (II) on Zeolite | He 500° C. | 9.6626 | Zn—O | 4.0 | 1.92 | 0.005 | −1.4 |
| (Catalyst 2) | $H_2$ 200° C. | 9.6626 | Zn—O | 3.9 | 1.94 | 0.005 | 1.2 |
| | $H_2$ 550° C. | 9.6625 | Zn—O | 3.6 | 1.94 | 0.005 | −0.8 |

Based on the X-ray absorption spectra and fits, the active form of the catalyst is thought to be a single metal ion, i.e., an isolated Zn(II) ion or Ga(III) ion surrounded by four oxygen atoms where the metal ion is directly bonded to the support through a shared oxygen atom. As a result, the active catalyst for oligomerization has a +2 or +3 charge and a single metal-oxygen (M-O) bond that anchors the metal ion to the support. The active catalyst does not have M-O-M bonds. This is further illustrated through the representative structures provided in FIGS. 15A and 15B.

Figure 15A:
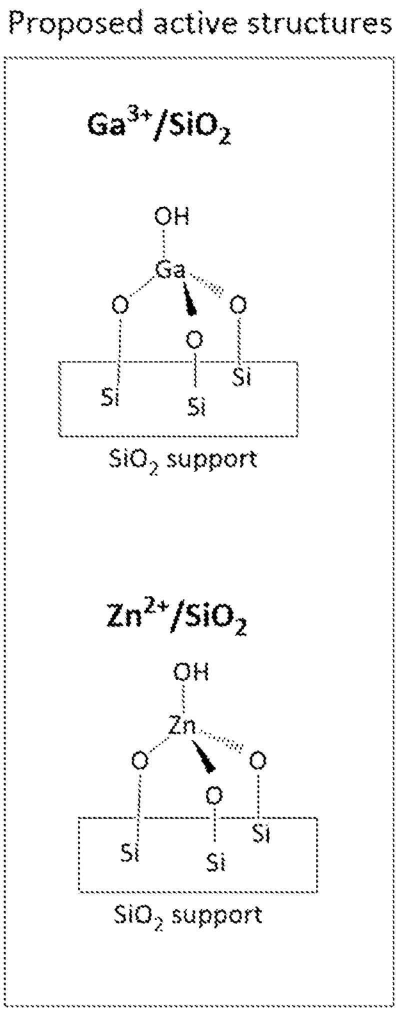
FIG. 15A depicts a representative structure for the single Zn(II) and Ga(III) metal ion centers grafted onto the surface of silica ($SiO_2$) through a shared oxygen atom. The resulting catalyst provides a single metal ion center with four M-O bonds which provide active sites for oligomerization in accordance with one or more embodiments described herein.
Figure 15B:
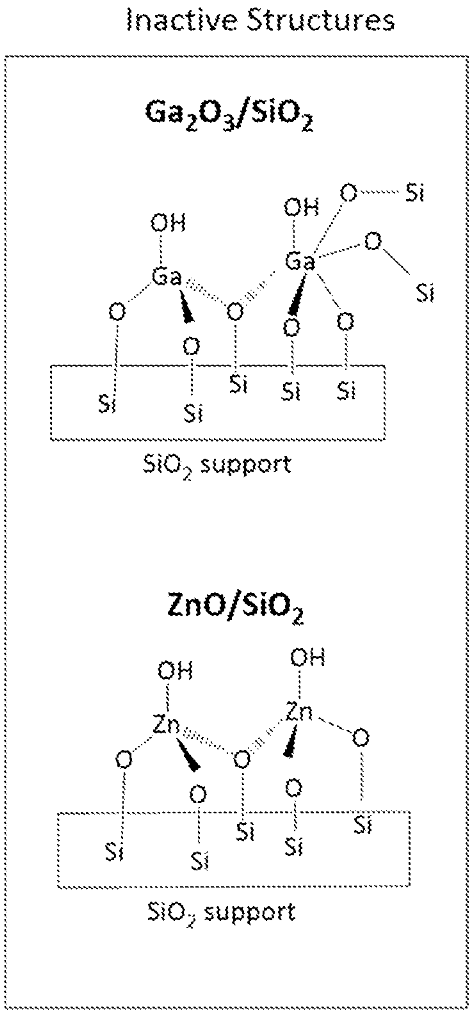
FIG. 15B depicts a representative structure for Zn(II) oxides and Ga(III) oxides grafted onto the surface of silica, forming M-O-M bonds that are not active for oligomerization.

FIG. 15A depicts a representative structure for the single Zn(II) and Ga(III) metal ion centers grafted onto the surface of silica ($SiO_2$) though a shared oxygen atom. The resulting catalyst provides up to four M-O bonds that can provide an active site for oligomerization. These inventive catalyst structures are in contrast to supported metal oxide catalysts containing M-O-M bonds, as depicted in FIG. 15B, which depicts a representative structure for Zn(II) oxides and Ga(III) oxides grafted onto the surface of silica, forming M-O-M bonds that are not active for oligomerization.

It has been surprisingly and unexpectedly discovered that supported single Zn(II) ion and Ga(III) ion metal catalysts can generate the same metal hydride reaction intermediate as the known Ni-based oligomerization catalysts and are active for oligomerization at temperatures of 200° C. or more. The metal hydride can be formed prior to reaction by pretreating the catalysts in $H_2$ or in situ in the absence of $H_2$ in the olefin reactor feed.

It was also surprisingly and unexpectedly discovered that the supported single Zn(II) ion and Ga(III) ion metal catalysts were regenerable. Prior to each reaction, both the Zn(II) and Ga(III) catalysts were white in color. After reaction, the catalysts turned beige or brown. The spent catalysts were calcined at 500° C. in flowing air for 3 hours, which restored the catalysts to their original white color and restored their catalytic activity to their original value.

Features of the present invention further relate to any one or more of the following embodiments.

1. An oligomerization catalyst, comprising a single Zn(II) metal ion center directly bonded to a support through a shared oxygen atom, the catalyst having at least one Zn—O bond which forms an active site for oligomerization.
2. The catalyst according to the preceding embodiment 1, wherein the zinc metal ion has a +2 oxidation state at a temperature of at least 200° C.
3. The catalyst according to the preceding embodiments 1 or 2, wherein zinc is present in an amount ranging from about 0.1 wt % to about 20 wt %, based on the total weight of the catalyst.
4. The catalyst according to any preceding embodiment 1 to 3, wherein the support has a surface area of about 30 m2/g to about 600 m2/g.
5. The catalyst according to any preceding embodiment 1 to 4, wherein the support has a pore size of about 5 Å to about 500 Å.
6. The catalyst according to any preceding embodiment 1 to 5, wherein the support is silica oxide, aluminum oxide or silica-aluminum oxide, zeolite, aluminum phosphate molecular sieve, silicon-aluminum phosphate molecular sieve, mesoporous molecular sieve.
7. A method for making light hydrocarbon oligomers, comprising: reacting one or more C2 to C12 olefins with a supported zinc catalyst at a temperature of about 200° C. or higher to provide an oligomer product comprising C4 to C26 olefins, wherein the supported zinc catalyst comprises a single Zn(II) metal ion center directly bonded to a support through a shared oxygen atom, the zinc is present in an amount ranging from about 0.1 wt % to about 20 wt %, based on the total weight of the catalyst.
8. The method according to the preceding embodiment 7, wherein the support material is silica having a pore size of about 5 Å to about 500 Å, and a surface area of about 25 m2/g to about 600 m2/g.
9. The method according to the preceding embodiments 7 or 8, wherein the one or more C2 to C12 olefins and supported zinc catalyst are reacted at a pressure of about 1 Bar(g) to about 100 Bar(g).
10. The method according to any preceding embodiment 7 to 9, wherein the one or more C2 to C12 olefins consist essentially of ethylene and propylene.
11. The method according to any preceding embodiment 7 to 10, wherein the oligomer product consists essentially of C4 to C26 olefins.
12. The method according to any preceding embodiment 7 to 11, wherein the oligomer product consists essentially of C12 to C20 olefins having a boiling point in the range of 170° C. to 360° C.
13. An oligomerization catalyst, comprising a single Ga(III) metal ion center directly bonded to a support through a shared oxygen atom, the catalyst having at least one Ga—O bond which forms an active site for oligomerization.
14. The catalyst according to the preceding embodiment 13, wherein the gallium metal ion has a +3 oxidation state at a temperature of at least 200° C.
15. The catalyst according to the preceding embodiments 13 or 14, wherein gallium is present in an amount ranging from about 2 wt % to about 20 wt %, based on the total weight of the catalyst.
16. The catalyst according to any preceding embodiment 13 to 15, wherein the support has a surface area of about 30 m2/g to about 600 m2/g.
17. The catalyst according to any preceding embodiment 13 to 16, wherein the support has a pore size of about 50 Å to about 500 Å.
18. The catalyst according to any preceding embodiment 13 to 17, wherein the support is silica oxide, aluminum oxide or silica-aluminum oxide.
19. A method for making light hydrocarbon oligomers, comprising: reacting one or more C2 to C12 olefins with a supported gallium containing catalyst at a temperature of about 200° C. or higher to provide an oligomer product comprising C4 to C26 olefins, wherein the supported gallium containing catalyst comprises a single Ga(III) metal ion center directly bonded to a support through a shared oxygen atom, the catalyst having at least one Ga—O bond which forms an active site for oligomerization, and the gallium is present in an amount ranging from about 2 wt % to about 20 wt %, based on the total weight of the catalyst.
20. The method according to the preceding embodiment 19, wherein the support material is silica having a pore size of about 50 Å to about 500 Å, and a surface area of about 100 m2/g to about 600 m2/g.
21. The method according to the preceding embodiments 19 or 20, wherein the one or more C2 to C12 olefins and supported gallium containing catalyst are reacted at a pressure of about 6.8 Bar(g) to about 138 Bar(g).
22. The method according to any preceding embodiment 19 to 21, wherein the one or more C2 to C12 olefins consist essentially of ethylene and propylene.

23. The method according to any preceding embodiment 19 to 22, wherein the oligomer product consists essentially of C4 to C26 olefins.

24. The method according to any preceding embodiment 19 to 23, wherein the oligomer product consists essentially of C12 to C20 olefins having a boiling point in the range of 170° C. to 360° C.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for making light hydrocarbon oligomers, comprising:
- contacting one or more C2 to C12 olefins with a supported zinc catalyst; and
- oligomerizing the one or more C2 to C12 olefins in the presence of the supported zinc catalyst to form an oligomer product comprising C4 to C26 olefins,
- wherein the supported zinc catalyst comprises a single Zn(II) metal ion center directly bonded to a support through a shared oxygen atom, and the zinc is present in an amount ranging from about 0.1 wt % to about 20 wt %, based on the total weight of the catalyst.

2. The method of claim 1, wherein the support material is silica having a pore size of about 5 Å to about 500 Å, and a surface area of about 25 m2/g to about 600 m2/g.

3. The method of claim 1, wherein the one or more C2 to C12 olefins and supported zinc catalyst are reacted at a pressure of about 1 Bar to about 100 Bar and temperature of about 135° C. to about 500° C.

4. The method of claim 1, wherein the one or more C2 to C12 olefins consist essentially of ethylene and propylene.

5. The method of claim 1, wherein the oligomer product consists of C4 to C26 olefins.

6. The method of claim 1, wherein the oligomer product consists essentially of C12 to C20 carbon atoms having a boiling point in the range of 170° C. to 360° C.

7. The method of claim 1, wherein the support has a surface area of about 30 m2/g to about 600 m2/g.

8. The method of claim 2, wherein the support has a pore size of about 50 Å to about 500 Å.

9. The method of claim 1, wherein the support is silica oxide, aluminum oxide or silica-aluminum oxide.

10. A method for making light hydrocarbon oligomers, comprising:
- contacting one or more C2 to C12 olefins with a supported zinc catalyst; and
- oligomerizing the one or more C2 to C12 olefins in the presence of the supported zinc catalyst to provide an oligomer product comprising C4 to C26 olefins, wherein the supported zinc catalyst comprises:
- a support; and
- at least one Zn(II) metal ion surrounded by four oxygen atoms, wherein:
- the at least one Zn(II) metal ion is directly bonded to the support through a shared oxygen atom to form at least one Zn(II)-O bond,
- the zinc metal ion center of the at least one Zn(II)-O bond has a +2 oxidation state at the reaction conditions, and
- the supported zinc catalyst does not have Zn—O—Zn bonds.

11. The method of claim 10, wherein the zinc is present in an amount ranging from about 0.1 wt % to about 20 wt %, based on the total weight of the catalyst.

12. The method of claim 10, wherein the support has a surface area of about 30 m2/g to about 600 m2/g.

13. The method of claim 10, wherein the support has a pore size of about 5 Å to about 500 Å.

14. The method of claim 10, wherein the support is silica oxide, aluminum oxide or silica-aluminum oxide, zeolite, aluminum phosphate molecular sieve, silicon-aluminum phosphate molecular sieve, mesoporous molecular sieve.

15. The method of claim 10, wherein the oligomer product has a boiling point in the range of 170° C. to 360° C.

16. A method for making light hydrocarbon oligomers, comprising:
- oligomerizing one or more C2 to C12 olefins in the presence of a catalyst at oligomerization conditions comprising a temperature of about 135° C. to about 500° C. and a pressure of about 1 bar to about 68.9 bar to provide an oligomer product comprising C4 to C26 olefins, wherein the catalyst comprises a zinc containing compound and a support comprising at least one oxygen atom, wherein:
- at least one Zn(II) metal ion is surrounded by four oxygen atoms,
- the at least one Zn(II) metal ion is directly bonded to the support through a shared oxygen atom to form at least one Zn(II)-O bond,
- the zinc metal ion center of the at least one Zn(II)-O bond has a +2 oxidation state at the reaction conditions, and
- the catalyst does not have Zn—O—Zn bonds.

17. The method of claim 16, wherein the zinc is present in an amount ranging from about 0.1 wt % to about 20 wt %, based on the total weight of the catalyst, the support has a surface area of about 30 m2/g to about 600 m2/g, and the support has a pore size of about 5 Å to about 500 Å.

18. The method of claim 17, wherein the support is silica oxide, aluminum oxide or silica-aluminum oxide, zeolite, aluminum phosphate molecular sieve, silicon-aluminum phosphate molecular sieve, mesoporous molecular sieve.

19. The method of claim 16, wherein the oligomer product has a boiling point in the range of 170° C. to 360° C.

20. The method of claim 16, wherein the one or more olefins are derived from natural gas, natural gas liquids, or mixtures of both.

* * * * *